United States Patent
Caldarelli et al.

(10) Patent No.: US 8,772,280 B2
(45) Date of Patent: Jul. 8, 2014

(54) N-ARYL-2-(2-ARYLAMINOPYRIMIDIN-4-YL) PYRROL-4-CARBOXAMIDE DERIVATIVES AS MPS1 KINASE INHIBITORS

(75) Inventors: Marina Caldarelli, Milan (IT); Stefano Adele Nuvoloni, Genoa (IT); Francesca Quartieri, Arona (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 239 days.

(21) Appl. No.: 13/260,665

(22) PCT Filed: Mar. 23, 2010

(86) PCT No.: PCT/EP2010/053779
§ 371 (c)(1),
(2), (4) Date: Sep. 27, 2011

(87) PCT Pub. No.: WO2010/108921
PCT Pub. Date: Sep. 30, 2010

(65) Prior Publication Data
US 2012/0065192 A1    Mar. 15, 2012

(30) Foreign Application Priority Data

Mar. 27, 2009  (EP) .................................. 09156449

(51) Int. Cl.
| | | |
|---|---|---|
| *A61K 31/55* | (2006.01) | |
| *A61K 31/497* | (2006.01) | |
| *A61K 31/505* | (2006.01) | |
| *C07D 243/08* | (2006.01) | |
| *C07D 403/04* | (2006.01) | |
| *C07D 401/04* | (2006.01) | |

(52) U.S. Cl.
USPC ...... 514/218; 514/252.19; 514/275; 540/575; 544/295; 544/331

(58) Field of Classification Search
USPC ..................... 514/218, 275, 252.19; 540/575; 544/295, 331
See application file for complete search history.

(56) References Cited

U.S. PATENT DOCUMENTS 8,426,417 B2 * 4/2013 Caruso et al. ............ 514/252.18
2012/0295906 A1 * 11/2012 Vanotti et al. .............. 514/235.5

FOREIGN PATENT DOCUMENTS

| WO | WO 2006/071644 A1 | 7/2006 |
| WO | WO 2007/110344 A1 | 10/2007 |
| WO | WO 2009/040399 A1 | 4/2009 |
| WO | WO 2009/156315 A1 | 12/2009 |

OTHER PUBLICATIONS

International Search Report dated Jun. 23, 2010 received from the European Patent Office from related International Application No. PCT/EP2010/053779.

* cited by examiner

*Primary Examiner* — Kamal Saeed
*Assistant Examiner* — Ebenezer O Sackey
(74) *Attorney, Agent, or Firm* — Scully, Scott, Murphy & Presser, P.C.

(57) ABSTRACT

The present invention relates to substituted pyrrolyl-pyrimidines which modulate the activity of protein kinases and are therefore useful in treating diseases caused by dysregulated protein kinase activity, in particular MPS1. The present invention also provides methods for preparing these compounds, pharmaceutical compositions comprising these compounds, and methods of treating diseases utilizing such these compounds or the pharmaceutical compositions containing them.

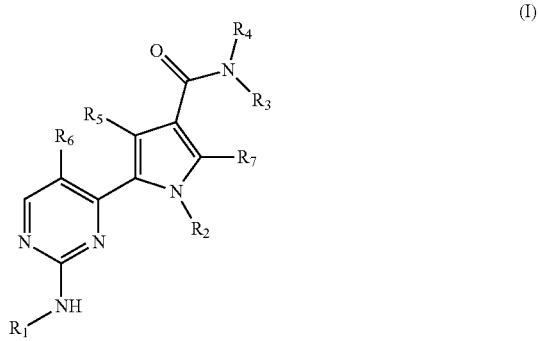

13 Claims, No Drawings

SEQUENCE LISTING

```
<160> NUMBER OF SEQ ID NOS: 2

<210> SEQ ID NO 1
<211> LENGTH: 80
<212> TYPE: DNA
<213> ORGANISM: Artificial Sequence
<220> FEATURE:
<223> OTHER INFORMATION: Forward primer

<400> SEQUENCE: 1
ggggacaagt ttgtacaaaa aagcaggctt actggaagtt ctgttccagg ggcccgaatc      60
cgaggattta agtggcagag                                                  80

<210> SEQ ID NO 2
<211> LENGTH: 74
<212> TYPE: DNA
<213> ORGANISM: Artificial Sequence
<220> FEATURE:
<223> OTHER INFORMATION: Reverse primer

<400> SEQUENCE: 2
ggggaccact ttgtacaaga aagctgggtt ttatttttt cccctttttt tttcaaaagt      60
cttggaggat gaag                                                        74
```

N-ARYL-2-(2-ARYLAMINOPYRIMIDIN-4-YL) PYRROL-4-CARBOXAMIDE DERIVATIVES AS MPS1 KINASE INHIBITORS

The present invention relates to substituted pyrrolyl-pyrimidines modulating the activity of protein kinases. The compounds of this invention are therefore useful in treating diseases caused by dysregulated protein kinase activity.

The present invention also provides methods for preparing these compounds, pharmaceutical compositions comprising them, and methods of treating diseases utilizing pharmaceutical compositions comprising these compounds.

The use of mitotic inhibitors in cancer therapy is a widely accepted clinical strategy for the treatment of a broad range of human cancers. Taxanes (Paclitaxel and Docetaxel) and Vinca Alkaloids (Vincristine and Vinblastine) work by either stabilizing or destabilizing microtubules with catastrophic consequences in cells progressing through mitosis. They are first line therapeutics for several tumor types and second line in cisplatin-refractory ovarian, breast, lung, bladder and esophagus cancers (Taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumor types. Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle.

The Spindle Assembly Checkpoint (SAC) is specifically required for proper chromosomal segregation into the two daughter cells upon cellular division. It ensures that sister chromatids aligned at the metaphase plate do not separate prior to the bipolar attachment of all duplicated chromosomes to the mitotic spindle (Reviewed in Musacchio A. and Salmon D. Nat Rev Mol Cell Biol, May; 8(5): 379-93, 2007).

Even a single un-aligned chromosome is sufficient to trigger the SAC signal, it is a tightly regulated pathway that ultimately results into the inhibition of the anaphase promoting complex/cyclosome (APC/C)-mediated polyubiquitylation and degradation of two key mitotic components: cyclin B1 and Securin. Securin specifically is required to get sister chromatids separation and anaphase transition, instead cyclin B1 inactivates the master mitotic kinase CDK1 promoting mitotic exit. (Reviewed in Musacchio A. and Salmon D. Nat Rev Mol Cell Biol, May; 8(5): 379-93, 2007).

A large group of proteins has already been identified to play a role in SAC functions: human MPS1 (monopolar spindle 1) kinase, (also known as TTK) has certainly a major role. MPS1 is a dual Tyrosine and Serine/Threonine kinase highly conserved from yeast to mammals. The human genome encodes for just one MPS1 gene family member, which does not have high sequence similarities with other protein kinases.

MPS1 is a cell cycle regulated enzyme that is upregulated and activated in mitosis upon phosphorylation (Stucke V M, et al., Embo J. 21 (7): 1723, 2002).

In *Saccharomyces cerevisiae*, MPS1 controls spindle-pole body duplication (Winey M. et al., J. Cell Biol 114:745, 1991), spindle assembly (Jones, M. H. et al., Curr. Biol. 15: 160, 2005) and the spindle assembly checkpoint (Weiss and Winey, J. Cell. Biol. 132: 111, 1996). Instead in higher eukaryotes the MPS1 kinase activity is mainly involved in SAC regulation and functions (Jelluma, N. et al., Cell 132: 233, 2008).

RNA interference experiments indicate that in the absence of MPS1 the SAC functions are compromised: mitotic length is reduced and cells divide rapidly without methaphase plate alignment, which ultimately causes aberrant aneuploidization, mitotic catastrophe and is not anymore compatible with cellular survival (Jelluma N. et al., Cell 132: 233, 2008; Tighe A. et al., J Cell Biol 2008; Jelluma N. et al., Plos ONE 3 (6): e2415, 2008). Moreover, to support these results, a small molecule ATP-competitor MPS1 inhibitor was described and despite its not clean selectivity profile, it was shown to be capable to inactivate SAC functions, inactivate nocodazole and taxol mediated mitotic arrest and promote cell death mainly in tumorigenic cell lines (Schmidt et al., EMBO Rep, 6(9): 866, 2005).

Despite most of the tumors are aneuploid, MPS1 was never found to be mutated in cancer, instead, it has been found upregulated in a number of tumors of different origins like bladder, anaplastic thyroid, breast and prostate cancer (Yuan B. et al, Clin Cancer Res, 12(2): 405-410). Moreover it was found in the signature of the top 25 genes over-expressed in CIN and aneuploid tumors which predict clinical outcome in breast and lung cancer, medulloblastoma, glioma, mesothelioma and lymphoma (Carter S L et al., Nat Genet. 38 (9): 1043, 2006). Finally it is highly elevated in metastatic tumors and was found to be over-expressed in p53 mutated breast cancers (Bertheau P. et al., Plos Med 4(3):e90, 2007).

Together with the fact that also other SAC components like MAD2, BUBR1 or BUB1 have been found up-regulated in different tumors (De Carcer G. et al., Curr Med Chem 14(9): 969, 2007), it looks that SAC functions could be required and essential to keep tumoral highly aneuploidy cells capable to segregate and tumoral selectivity of SAC inhibitors is foreseen in particular for highly aneuploid tumors like colon, lung and breast carcinomas (Kops G. J. et al., Nat. Rev Cancer, 5:773, 2005).

Finally, massive aneuploidy induction and SAC deregulation have been shown to reduce tumorigenesis in tumour prone mice sustaining the hypothesis that SAC inhibition could confer tumour growth inhibition (Weaver et al., Cancer Cell 11(1): 25, 2007).

Thus, for these reasons, pharmacological attenuation of MPS1 function may have a therapeutic benefit in the treatment of several diverse cancers.

Several pyrrolyl-pyrimidine derivatives for the treatment of hyperproliferative diseases such as cancer have been disclosed in WO 2006/071644 (Vertex Pharm Inc.), WO 2005/014572, WO 2007/068728 and WO 2007/071621 (Pfizer Italia Sri). WO2007/110344 in the name of the present Applicant, also describes and claims pyrrolyl-pyridine derivatives.

Despite these developments, there is still need for effective agents for said disease.

The present inventors have now discovered that compounds of formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a compound of the formula (I):

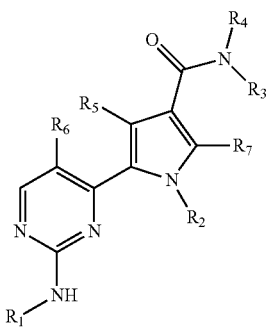

wherein $R_1$ is an aryl group;

$R_2$ is hydrogen atom or a group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl and heterocyclyl;

$R_3$ is an aryl group;

$R_4$ is hydrogen atom, hydroxyl or $C_1$-$C_6$ alkyl group, $C_2$-$C_6$ alkenyl, $C_2$-$C_6$ alkynyl, $C_3$-$C_7$ cycloalkyl and heterocyclyl, or, taken together with one of the atom of the group which $R_3$ represents, form a 5 to 8 membered cyclic group;

$R_5$, $R_6$ and $R_7$ are each independently hydrogen or halogen atom or a $C_1$-$C_6$ alkyl group;

wherein the groups aryl, heterocyclyl, $C_3$-$C_7$ cycloalkyl, straight or branched $C_1$-$C_6$ alkyl, straight or branched $C_2$-$C_6$ alkenyl, straight or branched $C_2$-$C_6$ alkynyl may be optionally substituted, provided that the compound 1-methyl-5-{2-[4-(1-methyl-piperidin-4-ylcarbamoyl)-2-trifluoromethoxy-phenylamino]-pyrimidin-4-yl}-1H-pyrrole-3-carboxylic acid o-tolylamide is excluded;

and stereoisomers, tautomers, hydrates, solvates, N-oxides and pharmaceutically acceptable salts thereof, The present invention also provides methods for synthesizing the compounds of the formula (I), prepared through a process consisting of standard synthetic transformations.

The present invention also provides a compound of formula (I) as defined above, for use as a medicament.

The present invention is also providing a compound of the formula (I) as defined above for the treatment of a disease caused by and/or associated with dysregulated protein kinase activity, human MPS1 (TTK), PLK family members, protein kinase C in different isoforms, Met, PAK-4, PAK-5, STLK-2, DDR-2, Aurora 1, Aurora 2, Bub-1, Chk1, Chk2, $HER_2$, raf1, MEK1, MAPK, EGF-R, PDGF-R, FGF-R, IGF-R, PI3K, wee1 kinase, Src, Abl, Akt, MAPK, ILK, MK-2, IKK-2, Cdc7, Nek, Cdk/cyclin kinase family, and more particularly human MPS1 which comprises administering to a mammal, in need thereof, an effective amount of a substituted pyrrolyl-pyrimidine compound represented by formula (I) as defined above.

Preferably, a compound of the formula (I) as defined above is used to treat a disease caused by and/or associated with dysregulated protein kinase activity selected from the group consisting of cancer, cell proliferative disorders, viral infections, autoimmune and neurodegenerative disorders.

Another preferred use of a compound of the formula (I) as defined above of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma mesothelioma, highly aneuploid tumors and tumors which do overexpress mitotic checkpoint components like MPS1, MAD2, MAD1, BUB1, BUBR1, BUB3 and others.

Another preferred use of a compound of the formula (I) as defined above of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

In addition, it is provided a compound of the formula (I) as defined above for use in tumor angiogenesis and metastasis inhibition as well as for the treatment of organ transplant rejection and host versus graft disease.

The present invention is also providing a method for treating diseases caused by and/or associated with an altered protein kinase activity as defined above which comprises administering to a mammal in need thereof an effective amount of a compound of the formula (I) as defined above.

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

The present invention further provides an in vitro method for inhibiting protein kinase activity which comprises contacting the kinase with an effective amount of a compound of formula (I) as defined above.

Unless otherwise specified, when referring to the compounds of formula (I) per se as well as to any pharmaceutical composition thereof or to any therapeutic treatment comprising them, the present invention includes all of the stereoisomers, tautomers, hydrates, solvates, N-oxides and pharmaceutically acceptable salts of the compounds of this invention.

N-oxides are compounds of formula (I) wherein nitrogen and oxygen are tethered through a dative bond.

If a stereogenic center or another form of an isomeric center is present in a compound of the present invention, all forms of such isomer or isomers, including enantiomers and diastereomers, are intended to be covered herein.

Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

When $R_4$ is taken together with one of the atom of the group which $R_3$ represents, they form a 5 to 8 membered cyclic group such as:

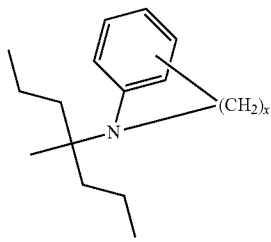

wherein x is an integer from 2 to 5.

With the term "aryl" we intend carbocyclic or heterocyclic groups containing from 1 to 2 ring moieties, either fused or linked to each other by single bonds, wherein at least one of the rings is aromatic; if present, any aromatic heterocyclic ring also referred to as heteroaryl group, comprises a 5 to 6 membered ring containing from 1 to 3 heteroatoms selected among N, NH, O or S. Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulphur. Non limiting examples of heterocyclic groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_3$-$C_7$ cycloalkyl" we intend, unless otherwise provided, 3- to 7-membered all-carbon monocyclic ring, which may contain one or more double bonds but does not have a completely conjugated π-electron system.

Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above group which $R_1$, $R_2$, $R_3$, $R_4$, $R_5$, $R_6$ and $R_7$ represent may be optionally substituted, in any of their free positions, by one or more groups, for instance 1 to 6 groups, independently selected from: halogen atom, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_6$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term halogen atom we intend a fluorine, chlorine, bromine or iodine atom.

With the term cyano we intend a —CN residue.

With the term nitro we intend a —NO_2 group.

With the term alkenyl or alkynyl we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term polyfluorinated alkyl or alkoxy we intend any of the above straight or branched $C_1$-$C_6$ alkyl or alkoxy groups which are substituted by more than one fluorine atom such as, for instance, trifluoromethyl, trifluoroethyl, 1,1,1,3, 3,3-hexafluoropropyl, trifluoromethoxy and the like.

With the term alkoxy, aryloxy, heterocyclyloxy and derivatives thereof we intend any of the above $C_1$-$C_6$ alkyl, aryl or heterocyclic groups linked to the rest of the molecule through an oxygen atom (—O—).

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_6$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of formula (I) also include the salts with inorganic or organic bases, e.g., alkali or alkaline-earth metals, especially sodium, potassium, calcium, ammonium or magnesium hydroxides, carbonates or bicarbonates, acyclic or cyclic amines, preferably methylamine, ethylamine, diethylamine, triethylamine, piperidine and the like.

Preferred compounds of formula (I) are the compounds wherein:

$R_1$ is an aryl of the formula:

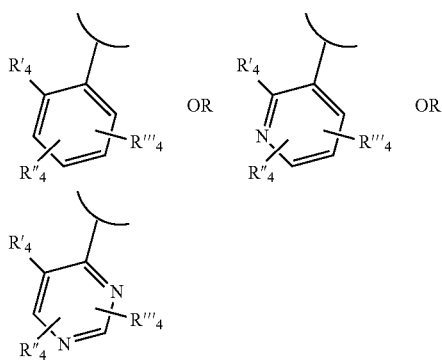

wherein $R'_4$, $R''_4$ and $R'''_4$ are independently hydrogen or halogen atom, or nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_6$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dial kylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate; more preferably in the above formulas $R'_4$ is not hydrogen atom.

Other preferred compounds are those wherein $R_1$ is an ortho-substituted-aryl group, that is an aryl group linked to the rest of the molecule through the —NH— moiety, said aryl group being substituted in ortho position with reference to the —NH— moiety, and also optionally substituted in any of the other positions.

A further preferred class of compounds of formula (I) are the compounds of formula (Ia):

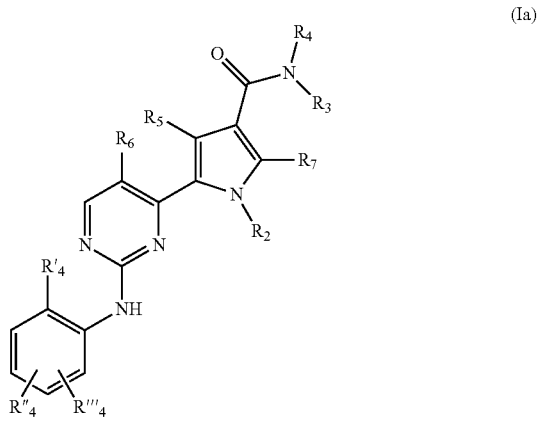

wherein $R_2$ is hydrogen atom or an optionally substituted straight or branched $C_1$-$C_6$ alkyl or $C_2$-$C_6$ alkenyl group;

$R_3$ is an optionally substituted aryl group;

$R_4$ is hydrogen atom, a $C_1$-$C_6$ alkyl or, taken together with one of the atom of the group which $R_3$ represents, form a 5 to 8 membered cyclic group;

$R'_4$, $R''_4$, $R'''_4$, $R_5$, $R_6$ and $R_7$ are as define above, or a pharmaceutically acceptable salt thereof.

Another particularly preferred class of compounds of the present invention are the compounds of formula (Ia) as defined above wherein $R_2$ is hydrogen or an optionally substituted straight or branched $C_1$-$C_6$ alkyl or $C_2$-$C_6$ alkenyl group;

$R_4$ is hydrogen atom, $C_1$-$C_6$ alkyl group or, taken together with one of the atom of the group which $R_3$ represents, form a 5 to 8 membered cyclic group;

$R_3$, $R'_4$, $R''_4$, and $R'''_4$ are as define above;

$R_5$, $R_6$ and $R_7$ are independently hydrogen or halogen atom, or a methyl group; or a pharmaceutically acceptable salt thereof.

Preferred specific compounds of formula (I) are the compounds listed below:

1) 5-[2-(4-Carbamoyl-2-methyl-phenylamino)-pyrimidin-4-yl]-1-methyl-1H-pyrrole-3-carboxylic acid (2,6-diethyl-phenyl)-amide;
2) 5-{2-[2-Methoxy-4-(4-methyl-piperazin-1-yl)-phenylamino]-pyrimidin-4-yl}-1-methyl-1H-pyrrole-3-carboxylic acid (2,6-diethyl-phenyl)-amide;
3) 1-Methyl-5-{2-[4-(1-methyl-piperidin-4-ylcarbamoyl)-2-trifluoromethoxy-phenylamino]-pyrimidin-4-yl}-1H-pyrrole-3-carboxylic acid phenylamide;
5) 5-[2-(4-tert-Butoxycarbonyl-2-methyl-phenylamino)-pyrimidin-4-yl]-1-methyl-1H-pyrrole-3-carboxylic acid ethyl ester;
6) 5-{2-[4-(2,6-Diethyl-phenylcarbamoyl)-2-methyl-phenylamino]-pyrimidin-4-yl}-1-methyl-1H-pyrrole-3-carboxylic acid (2,6-diethyl-phenyl)-amide;
7) 4-{4-[4-(2,6-Diethyl-phenylcarbamoyl)-1-methyl-1H-pyrrol-2-yl]-pyrimidin-2-ylamino}-3-methyl-benzoic acid;

8) 2-Chloro-5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

9) 2-Chloro-5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

10) 2-Chloro-5-{5-chloro-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

11) 2-Bromo-5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

12) 5-{5-Bromo-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

13) 2-Bromo-5-{5-bromo-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

14) 5-[2-(4-Dimethylcarbamoyl-2-methyl-phenylamino)-pyrimidin-4-yl]-1-methyl-1H-pyrrole-3-carboxylic acid (2,6-diethyl-phenyl)-amide;

15) 1-Methyl-5-[2-(2-methyl-4-methylcarbamoyl-phenylamino)-pyrimidin-4-yl]-1H-pyrrole-3-carboxylic acid (2,6-diethyl-phenyl)-amide;

16) 5-{2-[4-(2-Dimethylamino-ethylcarbamoyl)-2-methyl-phenylamino]-pyrimidin-4-yl}-1-methyl-1H-pyrrole-3-carboxylic acid (2,6-diethyl-phenyl)-amide;

17) 5-{2-[4-(4-Dimethylamino-piperidine-1-carbonyl)-2-methyl-phenylamino]-pyrimidin-4-yl}-1-methyl-1H-pyrrole-3-carboxylic acid (2,6-diethyl-phenyl)-amide;

18) 1-Methyl-5-{2-[2-methyl-4-((R)-2-pyrrolidin-1-ylmethyl-pyrrolidine-1-carbonyl)-phenylamino]-pyrimidin-4-yl}-1H-pyrrole-3-carboxylic acid (2,6-diethyl-phenyl)-amide;

19) 5-[2-(4-Carbamoyl-2-methyl-phenylamino)-pyrimidin-4-yl]-2-chloro-1-methyl-1H-pyrrole-3-carboxylic acid (2,6-diethyl-phenyl)-amide;

20) 5-[2-(4-Carbamoyl-2-methyl-phenylamino)-5-chloro-pyrimidin-4-yl]-1-methyl-1H-pyrrole-3-carboxylic acid (2,6-diethyl-phenyl)-amide;

21) 5-[2-(4-Carbamoyl-2-methyl-phenylamino)-5-chloro-pyrimidin-4-yl]-2-chloro-1-methyl-1H-pyrrole-3-carboxylic acid (2,6-diethyl-phenyl)-amide;

22) 5-[2-(4-Carbamoyl-2-methyl-phenylamino)-pyrimidin-4-yl]-4-chloro-1-methyl-1H-pyrrole-3-carboxylic acid (2,6-diethyl-phenyl)-amide;

23) 5-[2-(4-Bromo-2-methoxy-phenylamino)-pyrimidin-4-yl]-1-methyl-1H-pyrrole-3-carboxylic acid (2,6-diethyl-phenyl)-amide;

24) 5-{2-[4-(4-Dimethylamino-piperidin-1-yl)-2-methoxy-phenylamino]-pyrimidin-4-yl}-1-methyl-1H-pyrrole-3-carboxylic acid (2,6-diethyl-phenyl)-amide;

25) 5-[2-(2-Methoxy-phenylamino)-pyrimidin-4-yl]-1-methyl-1H-pyrrole-3-carboxylic acid (2,6-diethyl-phenyl)-amide;

26) 5-{2-[2-Methoxy-4-(4-methyl-[1,4]diazepan-1-yl)-phenylamino]-pyrimidin-4-yl}-1-methyl-1H-pyrrole-3-carboxylic acid (2,6-diethyl-phenyl)-amide;

27) 4-{4-[4-(2,6-Diethyl-phenylcarbamoyl)-1-methyl-1H-pyrrol-2-yl]-5-methyl-pyrimidin-2-ylamino}-3-methyl-benzoic acid tert-butyl ester;

28) 5-(2-{4-[(2-Dimethylamino-ethyl)-methyl-amino]-2-methoxy-phenylamino}-pyrimidin-4-yl)-1-methyl-1H-pyrrole-3-carboxylic acid (2,6-diethyl-phenyl)-amide;

29) 4-{4-[4-(2,6-Diethyl-phenylcarbamoyl)-1-methyl-1H-pyrrol-2-yl]-5-methyl-pyrimidin-2-ylamino}-3-methyl-benzoic acid;

30) 5-[2-(4-Carbamoyl-2-methyl-phenylamino)-5-methyl-pyrimidin-4-yl]-1-methyl-1H-pyrrole-3-carboxylic acid (2,6-diethyl-phenyl)-amide;

31) 5-{2-[4-(4-Dimethylamino-piperidine-1-carbonyl)-2-methyl-phenylamino]-5-methyl-pyrimidin-4-yl}-1-methyl-1H-pyrrole-3-carboxylic acid (2,6-diethyl-phenyl)-amide;

32) 5-(2-{4-[(3-Dimethylamino-propyl)-methyl-amino]-2-methoxy-phenylamino}-pyrimidin-4-yl)-1-methyl-1H-pyrrole-3-carboxylic acid (2,6-diethyl-phenyl)-amide;

33) 5-[2-(4-Bromo-2-methoxy-phenylamino)-5-chloro-pyrimidin-4-yl]-1-(2,2,2-trifluoro-ethyl)-1H-pyrrole-3-carboxylic acid (2,6-diethyl-phenyl)-amide;

34) 1-(2-Fluoro-ethyl)-5-{2-[2-methoxy-4-(4-methyl-piperazin-1-yl)-phenylamino]-pyrimidin-4-yl}-1H-pyrrole-3-carboxylic acid (2,6-diethyl-phenyl)-amide;

35) 5-{5-Bromo-2-[2-methoxy-4-(4-methyl-piperazin-1-yl)-phenylamino]-pyrimidin-4-yl}-1-methyl-1H-pyrrole-3-carboxylic acid (2,6-diethyl-phenyl)-amide;

36) 5-(2-{4-[4-(2-Hydroxy-ethyl)-piperazin-1-yl]-2-methoxy-phenylamino}-pyrimidin-4-yl)-1-methyl-1H-pyrrole-3-carboxylic acid (2,6-diethyl-phenyl)-amide;

37) 5-{2-[2-Methoxy-4-(4-methyl-piperazin-1-yl)-phenylamino]-pyrimidin-4-yl}-1-methyl-1H-pyrrole-3-carboxylic acid (2-chloro-6-methyl-phenyl)-amide;

38) 5-[2-(4-Bromo-2-methyl-phenylamino)-pyrimidin-4-yl]-1-methyl-1H-pyrrole-3-carboxylic acid (2,6-diethyl-phenyl)-amide;

39) 1-Methyl-5-{2-[2-methyl-4-(4-methyl-piperazin-1-yl)-phenylamino]-pyrimidin-4-yl}-1H-pyrrole-3-carboxylic acid (2,6-diethyl-phenyl)-amide;

40) 5-{2-[4-(4-Dimethylamino-piperidin-1-yl)-2-methyl-phenylamino]-pyrimidin-4-yl}-1-methyl-1H-pyrrole-3-carboxylic acid (2,6-diethyl-phenyl)-amide;

41) 1-Methyl-5-(2-o-tolylamino-pyrimidin-4-yl)-1H-pyrrole-3-carboxylic acid (2,6-diethyl-phenyl)-amide;

42) 5-{2-[2-Methoxy-4-(4-methyl-piperazin-1-yl)-phenylamino]-pyrimidin-4-yl}-1-methyl-1H-pyrrole-3-carboxylic acid (2,6-dimethyl-phenyl)-amide;

43) 5-{2-[2-Methoxy-4-(4-methyl-piperazin-1-yl)-phenylamino]-pyrimidin-4-yl}-1-methyl-1H-pyrrole-3-carboxylic acid (2-ethyl-6-methyl-phenyl)-amide;

44) 5-{2-[2-Methoxy-4-(4-methyl-piperazin-1-yl)-phenylamino]-pyrimidin-4-yl}-1-methyl-1H-pyrrole-3-carboxylic acid (2-methoxy-6-methyl-phenyl)-amide;

45) 5-{2-[2-Methoxy-4-(4-methyl-piperazin-1-yl)-phenylamino]-pyrimidin-4-yl}-1-methyl-1H-pyrrole-3-carboxylic acid (2-bromo-6-methyl-phenyl)-amide;

46) 5-{2-[2-Methoxy-4-(4-methyl-piperazin-1-yl)-phenylamino]-pyrimidin-4-yl}-1-methyl-1H-pyrrole-3-carboxylic acid (2,6-difluoro-phenyl)-amide;

47) 5-{2-[2-Methoxy-4-(4-methyl-piperazin-1-yl)-phenylamino]-pyrimidin-4-yl}-1-methyl-1H-pyrrole-3-carboxylic acid (2,4,6-trimethyl-phenyl)-amide;

48) 5-{2-[2-Methoxy-4-(4-methyl-piperazin-1-yl)-phenylamino]-pyrimidin-4-yl}-1-methyl-1H-pyrrole-3-carboxylic acid (2,4-dimethyl-pyridin-3-yl)-amide;

49) 5-{2-[2-Methoxy-4-(4-methyl-piperazin-1-yl)-phenylamino]-pyrimidin-4-yl}-1-methyl-1H-pyrrole-3-carboxylic acid (4-bromo-2-chloro-6-methyl-phenyl)-amide;

50) 5-{2-[2-Methoxy-4-(4-methyl-piperazin-1-yl)-phenylamino]-pyrimidin-4-yl}-1-methyl-1H-pyrrole-3-carboxylic acid (4-bromo-2,6-diethyl-phenyl)-amide;

51) 5-{2-[2-Methoxy-4-(4-methyl-piperazin-1-yl)-phenylamino]-pyrimidin-4-yl}-1-methyl-1H-pyrrole-3-carboxylic acid (3-chloro-2,6-diethyl-phenyl)-amide;

52) 5-{2-[2-Methoxy-4-(4-methyl-piperazin-1-yl)-phenylamino]-pyrimidin-4-yl}-1-methyl-1H-pyrrole-3-carboxylic acid (2,6-diethyl-4-methyl-phenyl)-amide;

53) 5-{2-[2-Methoxy-4-(4-pyrrolidin-1-yl-piperidin-1-yl)-phenylamino]-pyrimidin-4-yl}-1-methyl-1H-pyrrole-3-carboxylic acid (2,6-diethyl-phenyl)-amide;

54) 5-{2-[2-Methoxy-4-(1-methyl-piperidin-4-ylamino)-phenylamino]-pyrimidin-4-yl}-1-methyl-1H-pyrrole-3-carboxylic acid (2,6-diethyl-phenyl)-amide;

55) 5-{2-[4-(2-Dimethylamino-ethylamino)-2-methoxy-phenylamino]-pyrimidin-4-yl}-1-methyl-1H-pyrrole-3-carboxylic acid (2,6-diethyl-phenyl)-amide and 56) 1-Methyl-5-{2-[4-(1-methyl-piperidin-4-ylcarbamoyl)-2-trifluoromethoxy-phenylamino]-pyrimidin-4-yl}-1H-pyrrole-3-carboxylic acid (2,6-diethyl-phenyl)-amide.

For a reference to any specific compound of formula (I) of the invention, optionally in the form of a pharmaceutically acceptable salt, see the experimental section and claims.

The present inventions also provides processes for the preparation of a compound of the formula (I) as defined above, which are depicted in the following scheme:

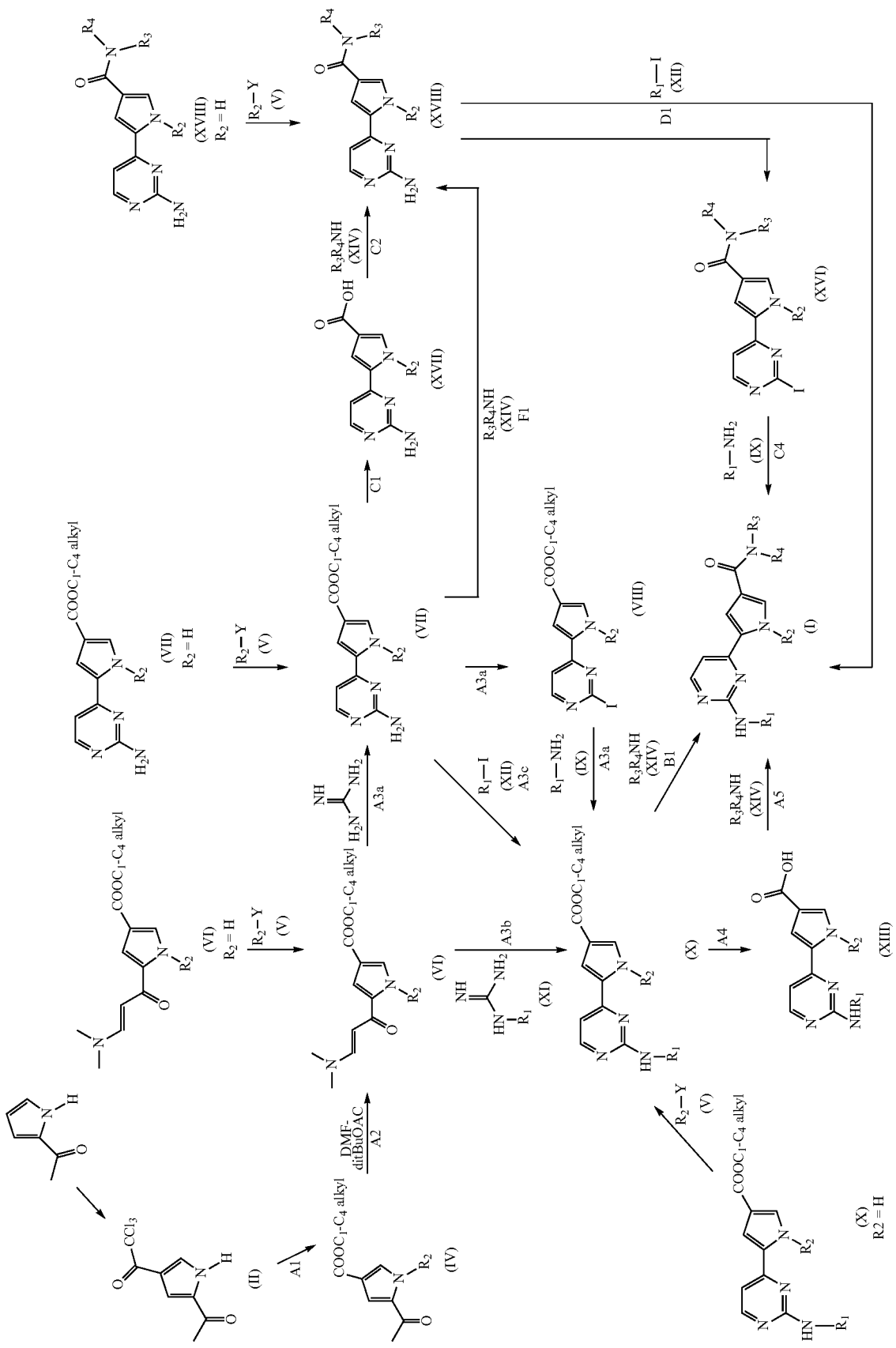

A first process according to the present invention comprises:

st.A1) reacting a compound of the formula (II):

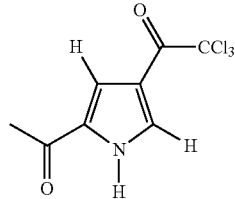
(II)

with a base in a $C_1$-$C_4$ alcohol like potassium carbonate in ethanol;

st.A2) reacting the resultant compound of formula (IV):

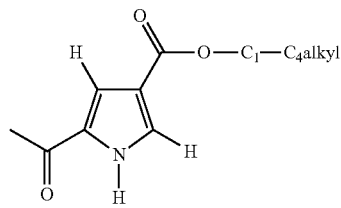
(IV)

with dimethylformamide-di-tert-butylacetale, dimethylformamide-diisopropylacetale or dimethylformamide-diethylacetale;

optionally converting the resultant compound of the formula (VI):

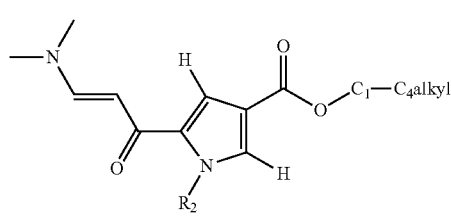
(VI)

wherein $R_2$ is H, by means of alkylation with a compound of the formula (V):

—Y (V)

wherein Y is a suitable leaving group such as mesyl or tosyl group, or halogen atom, and $R_2$ is as defined above but not hydrogen, into a different compound of the formula (VI) wherein $R_2$ is not hydrogen atom;

st.A3) reacting the compound of the formula (VI) as defined above according to one of the the following alternative steps (st.A3a), (st.A3b) or (st. A3c):

st.A3a) either with guanidine and then reacting the resultant compound of the formula (VII):

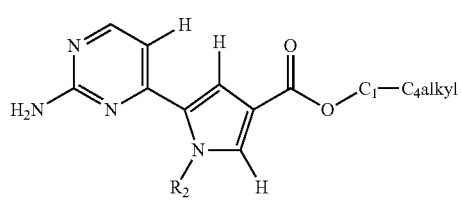
(VII)

wherein $R_2$ is as defined above, with iso-amylnitrite and diiodomethane or cesium iodide, in the presence of iodine and CuI, and then reacting the resultant compound of the formula (VIII):

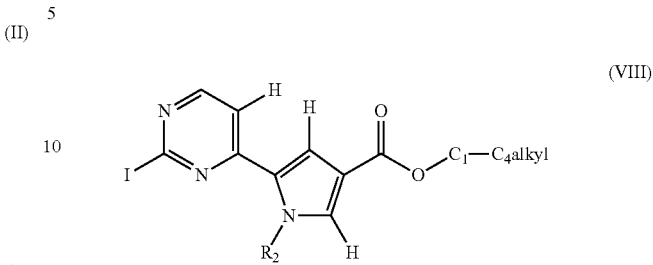
(VIII)

wherein $R_2$ is as defined above with a compound of formula (IX): $R_1$—$NH_2$ wherein $R_1$ is as defined above;

st.A3b) or with a guanidine derivative of formula (XI):

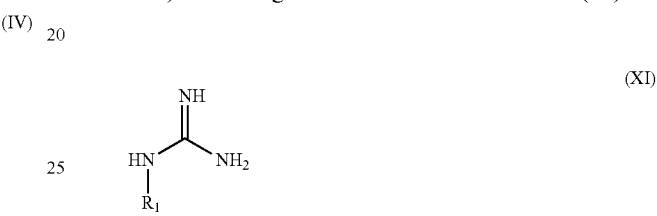
(XI)

wherein $R_1$ is as defined above;

st.A3c) with guanidine, and then reacting the resultant compound of the formula (VII) as defined above with a compound of the formula (XII): $R_1$—I wherein $R_1$ is as defined above;

st.A4) reacting the resultant compound of the formula (X):

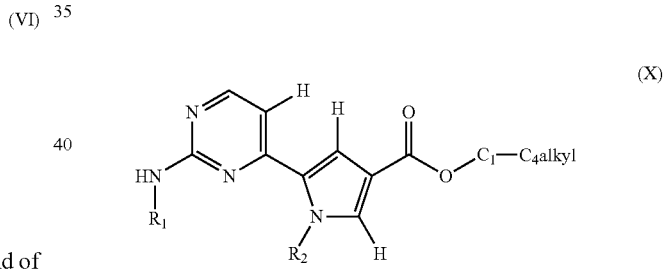
(X)

wherein $R_1$ and $R_2$ are as defined above in acidic or basic condition;

st.A5) reacting the resultant compound of the formula (XIII) or a salt thereof:

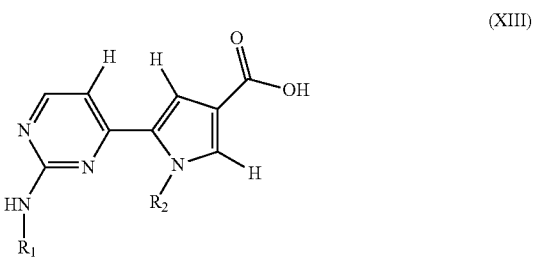
(XIII)

wherein $R_1$ and $R_2$ are as defined above, with an amine of the formula (XIV):

$R_3$—NH—$R_4$ (XIV)

wherein R₃ and R₄ are as defined above, in presence of the suitable condensing agents; and optionally converting the resultant compound of the formula (I):

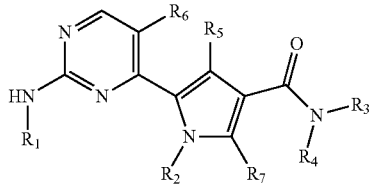

(I)

wherein R₁, R₂, R₃ and R₄ are as defined above and R₅, R₆ and R₇ are hydrogen atoms, into a a different compound of the formula (I); and, if desired, converting a compound of formula (I) into a pharmaceutically acceptable salt thereof or converting a salt into the free compound (I).

Another process according to the present invention comprises:

st.B1) reacting a compound of formula (X) as define above with an amine of the formula (XIV) as defined above, in presence of a strong base, and optionally converting the resultant compound of the formula (I) as defined above wherein R₅, R₆ and R₇ are hydrogen atoms, into a a different compound of the formula (I); and, if desired, converting a compound of formula (I) into a pharmaceutically acceptable salt thereof or converting a salt into the free compound(I).

A further process according to the present invention comprises:

st.C1) reacting a compound of the formula (VII) as define above in acidic or basic conditions;

st.C2) reacting the resultant compound of the formula (XVII) or a salt thereof:

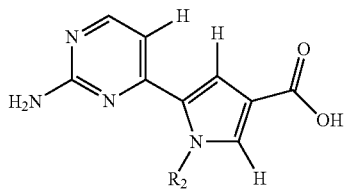

(XVII)

wherein R₂ is as define above with an amine of the formula (XIV) as defined above, in presence of the suitable condensing agents;

st.C3) reacting the resultant compound of the formula (XVIII):

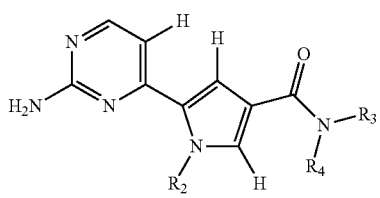

(XVIII)

wherein R₂, R₃ and R₄ are as define above with iso-amylnitrite and diiodomethane or cesium iodide, in the presence of iodine and CuI;

st.C4) reacting the resultant compound of the formula (XVI):

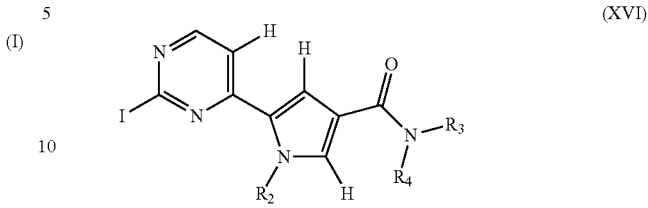

(XVI)

wherein R₂, R₃ and R₄ are as define above, with an with an arylamine of formula (IX) as defined above;

and optionally converting the resultant compound of the formula (I) as defined above wherein R₅, R₆ and R₇ are hydrogen atoms, into a different compound of the formula (I); and, if desired, converting a compound of formula (I) into a pharmaceutically acceptable salt thereof or converting a salt into the free compound (I).

A further process according to the present invention comprises:

st.D1) reacting a compound of (XVIII) as defined above a with a compound of the formula (XII) as defined above, and optionally converting the resultant compound of the formula (I) as defined above wherein R₅, R₆ and R₇ are hydrogen atoms, into a different compound of the formula (I); and, if desired, converting a compound of formula (I) into a pharmaceutically acceptable salt thereof or converting a salt into the free compound (I).

A further process according to the present invention comprises:

st.F1) reacting a compound of formula (VII) as defined above with an amine of formula (XIV) as defined above, in presence of a strong base, and then converting the resultant compound of the formula (XVIII) as defined above into a compound of the formula (I) as defined above wherein R₅, R₆ and R₇ are hydrogen atoms, or a pharmaceutically salt thereof, as described above under steps st.C3) and st.C4) or st.D1), and optionally converting the resultant compound of the formula (I) as defined above wherein R₅, R₆ and R₇ are hydrogen atoms, into a different compound of the formula (I); and, if desired, converting a compound of formula (I) into a pharmaceutically acceptable salt thereof or converting a salt into the free compound (I).

A compound of the formula (VII), (X) or (XVIII) wherein R₂ is hydrogen can be converted into the corresponding compounds having R₂ different from H by reaction with a suitable compound of formula R₂—Y (V) as defined above (conv.a).

As stated above, the compounds of formula (I) prepared as described above can be optionally and conveniently converted into other compounds of formula (I) by operating according to well-known synthetic conditions, the following being examples of possible conversions:

conv.b and c) converting a compound of formula (I) wherein R₂ is hydrogen and R₁, R₃, R₄, R₅ and R₆ are as defined above into a compound of formula (I) wherein R₂ is as defined above but not hydrogen by reaction either with a compound of the formula (V) as defined above, or with an alcohol of formula R₂—OH (XIX) wherein R₂ is as defined above but not hydrogen;

conv.d) converting a compound of the formula (Ia) wherein one of R′₄, R″₄ or R‴₄ is Br, into a compound of formula (Ia) wherein one of R′₄, R″₄ or R‴₄ is a group of the formula —NR₈R₉ wherein R₈ and R₉ are each independently selected from a group consisting of: hydrogen atom, $C_1$-$C_6$ alkyl, polyfluorinated alkyl, alkenyl, alkynyl, hydroxyalkyl, aryl, arylalkyl, heterocyclyl, $C_3$-$C_6$ cycloalkyl, alkylamino, arylamino, heterocyclyamino, by treatment with an amine of the formula $R_8R_9$—NH (XV), wherein $R_8$ and $R_9$ are as defined above;

conv.e) converting a compound of formula (Ia) wherein one of $R'_4$, $R''_4$ or $R'''_4$ is a nitro group into a compound of formula (Ia) wherein one of $R'_4$, $R''_4$ or $R'''_4$, is an amino group (—$NH_2$), by conventional methods of reduction;

cony.f) converting a compound of formula (Ia) wherein one of $R'_4$, $R''_4$ or $R'''_4$ is an amino group (—$NH_2$), into a compound of formula (Ia) wherein one of $R'_4$, $R''_4$ or $R'''_4$ is a group —$NHCOR_{10}$, wherein $R_{10}$ is selected from a group consisting of: $C_1$-$C_6$ alkyl, polyfluorinated alkyl, alkenyl, alkynyl, aryl, arylalkyl, heterocyclyl, $C_3$-$C_6$ cycloalkyl, alkylamino, arylamino, heterocyclyamino, by treatment with an acid of the formula $R_{10}$—COOH (XX), wherein $R_{10}$ is as defined above, in the presence of suitable condensing agents;

conv.g) converting a compound of formula (Ia) wherein one of $R'_4$, $R''_4$ or $R'''_4$ is t-butyloxycarbonyl in acidic condition, into a compound of formula (Ia) wherein one of $R'_4$, $R''_4$ or $R'''_4$ is —COOH;

conv.h) converting a compound of formula (Ia) wherein one of $R'_4$, $R''_4$ or $R'''_4$ is COOH, into a compound of formula (Ia) wherein one of $R'_4$, $R''_4$ or $R'''_4$ is a group —$CONR_8R_9$ wherein $R_8$ and $R_9$ are as defined above, by treatment with an amine of the formula (XV) as defined above in the presence of the suitable condencing agents;

conv.i) converting a compound of formula (I) wherein $R_5$, $R_6$ and $R_7$ are hydrogen atoms into a compound of formula (I) wherein one or more of $R_5$, $R_6$ and $R_7$ are halogen atoms, by reaction with N-halogensuccinimide;

conv.l) converting a compound of formula (I) wherein one or more of $R_5$, $R_6$ and $R_7$ are halogen into a compound of formula (I) wherein one or more of $R_5$, $R_6$ and $R_7$ are a $C_1$-$C_6$ alkyl group, by treatment with a suitable organo metallic a compounds, such as for example AlMe3.

In analogous way, when $R_1$ represents an aryl group of the formula:

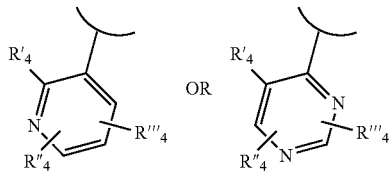

the same conversions d), e), f), g) and h) can be carried out.

According to step (st.A1) of the process, the compound of formula (II) is reacted with potassium carbonate in the presence of ethanol, so as a compound of formula (IV) is obtained. The reaction is preferably carried out at room temperature.

As stated above, any of the compounds of the formula (VI), (X), (XVIII) or (I) wherein $R_2$ is hydrogen can be reacted with a suitable compound of formula $R_2$—Y (V) wherein $R_2$ is as defined above but not hydrogen and Y is halogen preferably chlorine, bromine or iodine so as to obtain the corresponding compounds wherein $R_2$ is as defined above but not hydrogen. The reaction is carried out in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C.

According to step (st.A2) of the process, the reaction of the compound of formula (IV) with dimethylformamide-di-tert-butylacetale, dimethylformamide-diisopropylacetale or dimethylformamide-diethylacetale is carried out in the presence of a suitable solvent such as, for instance, dimethylformamide, so as to get the compounds of formula (VI). Preferably, the reaction is carried out at a temperature ranging from room temperature to about 80° C.

Optionally, the compound of formula (VI) wherein $R_2$ is hydrogen, is reacted with a suitable compound of formula $R_2$—Y (V) wherein $R_2$ is as defined above but not hydrogen and Y is halogen preferably chlorine, bromine or iodine in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., so as to obtain compound (VI) wherein $R_2$ is as defined above but not hydrogen.

According to step (st.A3a) of the process, the compound of formula (VI) is reacted with guanidine or guanidine salts as to obtain a compound of formula (VII) through pyrimidine ring formation. Compounds of formula (X), can be obtained by the corresponding iodo-derivatives of formula (VIII) which, in their turn, is prepared by the corresponding compounds of formula (VII).

Optionally, the compound of formula (VII) wherein $R_2$ is hydrogen, is reacted with a suitable compound of formula $R_2$—Y (V) wherein $R_2$ is as defined above but not hydrogen and Y is halogen preferably chlorine, bromine or iodine in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., so as to obtain compound (VII) wherein $R_2$ is as defined above but not hydrogen.

The preparation of the iodo-derivatives of formula (VIII) may be carried out in a suitable solvent such as tetrahydrofuran, diethyl ether or dimethoxyethane, at a temperature ranging from room temperature to about 80° C., and for a time of about 2 to about 48 hours.

The subsequent conversion of the iodo-derivative of formula (VIII) into compounds of formula (X) may be carried out in the presence of an amine of formula (IX) in a suitable solvent such as dimethylformamide, dimethoxyethane or acetonitrile and in the presence of catalytic amounts of palladium acetate, 2,2'-bis(diphenylphosphino)-1,1'-binaphtalene (BINAP) and a base such as potassium carbonate, potassium phosphate or cesium carbonate, at a temperature ranging from room temperature to 110° C. and for a time ranging from about 2 to about 24 hours.

Optionally, the compound of formula (X) wherein $R_2$ is hydrogen, is reacted with a suitable compound of formula $R_2$—Y (V) wherein $R_2$ is as defined above but not hydrogen and Y is halogen preferably chlorine, bromine or iodine in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., so as to obtain compound (X) wherein $R_2$ is as defined above but not hydrogen.

According to step (st.A3b) of the process, the compound of formula (VI) is reacted with guanidine derivatives of formula (XI) to obtain the corresponding compound of formula (X) through pyrimidine ring formation. Any of the above reactions are carried out according to conventional methods. As an example, the reactions with guanidine or salts thereof such as hydrochloride, carbonate or nitrate, or with the guanidine derivative of formula (XI), as set forth in steps (st.3a) or (st.3b), are carried out in a suitable solvent like dimethylformamide at a temperature ranging from 80° C. to refluxing temperature eventually in the presence of potassium carbonate or potassium tert-butylate.

According to step (st. A3c) of the process, the compound of formula (VII) is reacted with compounds of formula (XII), according to conventional methods. As an example the reaction can be carried out in a suitable solvent such as dimethylformamide, dimethoxyethane or acetonitrile and in the presence of an ortho-substituted-aryliodine of formula (XII), catalytic amounts of palladium acetate or tris(dibenzylideneacetone)dipalladium ($Pd_2(dba)_3$), 2,2'-bis(diphenylphosphino)-1,1'-binaphtalene (BINAP) or 2-(dicyclohexylphosphino)-2',4',6'-triisopropyl-1,1-biphenyl (X-phos) and a base such as potassium carbonate, potassium phosphate or cesium carbonate, at a temperature ranging from room temperature to 110° C. and for a time ranging from about 2 to about 24 hours.

According to step (st.A4) of the process, the compounds of formula (X) may be converted into carboxylic acid derivatives of formula (XIII) or corresponding salt through basic or acidic hydrolysis conditions, widely known in the art.

According to step (st.A5) of the process compounds of formula (XIII) may be converted into carboxamido derivatives of formula (I) wherein $R_3$ and $R_4$ are as defined above. The reaction is carried out with an amine of formula (XIV), under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required; at a temperature ranging from room temperature to 80° C. and for a time ranging from about 2 to about 24 hours.

According to step (st.B1) of the process, the compound of formula (X) may be converted into carboxamido derivatives of formula (I) wherein $R_3$ and $R_4$ are as defined above. The reaction is carried out with an amine of formula (XIV), under basic conditions, preferably with lithium bis(trimethylsilyl)amide or sodium bis(trimethylsilyl)amide, in a suitable solvent such as tetrahydrofuran, or dioxane; at a temperature ranging from 0 ° C. to 40° C. and for a time ranging from about 1 to about 24 hours.

According to step (st.C1) of the process, the compounds of formula (VII) may be converted into carboxylic acid derivatives of formula (XVII) or corresponding salt through basic or acidic hydrolysis conditions, widely known in the art.

According to step (st.C2) of the process compounds of formula (XVII) may be converted into carboxamido derivatives of formula (XVIII) wherein $R_3$ and $R_4$ are as defined above. The reaction is carried out in presence of amine of formula (XIV), under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required.

Optionally, the compound of formula (XVIII) wherein $R_2$ is hydrogen, is reacted with a suitable compound of formula $R_2$—Y (V) wherein $R_2$ is as defined above but not hydrogen and Y is halogen preferably chlorine, bromine or iodine in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., so as to obtain compound (XVIII) wherein $R_2$ is as defined above but not hydrogen.

According to step (st.C3) of the process compounds of formula (XVIII) may be converted into derivatives of formula (XVI) wherein $R_2$, $R_3$, $R_4$, $R_5$ and $R_6$ are as defined above. The reaction is carried out in a suitable solvent such as dimethoxyethane, tetrahydrofuran or diethyl ether in presence of cesium iodide, iodine, copper iodide and isopentyl nitrite at a temperature ranging from 50 to 80° C. and for a time ranging from about 2 to about 24 hours.

According to step (st.C4) of the process, the compound of formula (XVI) is converted into a compound of formula (I) wherein $R_1$, $R_2$, $R_3$, $R_4$a, $R_5$ and $R_6$ are as defined above, by reaction with an amine of formula $R_1NH_2$ (IX). The reaction is carried out in presence of the amine (IX) in a suitable solvent such as dimethylformamide, dimethoxyethane or acetonitrile and in the presence of catalytic amounts of palladium acetate, 2,2'-bis(diphenylphosphino)-1,1'-binaphtalene (BINAP) and a base such as potassium carbonate, potassium phosphate or cesium carbonate, at a temperature ranging from room temperature to 110° C. and for a time ranging from about 2 to about 24 hours.

According to step (st.D1) of the process, the compound of formula (XVIII) as defined above is reacted with compounds of the formula (XII) as defined above, according to conventional methods. As an example the reaction can be carried out in a suitable solvent such as dimethylformamide, dimethoxyethane or acetonitrile and in the presence of an ortho-substituted-aryliodine of the formula (XII) as defined above, catalytic amounts of palladium acetate or tris(dibenzylideneacetone)dipalladium ($Pd_2(dba)_3$), (2,2'-bis(diphenylphosphino)-1,1'-binaphtalene (BINAP) or 2-(dicyclohexylphosphino)-2',4',6'-triisopropyl-1,1'-biphenyl (X-phos) and a base such as potassium carbonate, potassium phosphate or cesium carbonate, at a temperature ranging from room temperature to 110° C. and for a time ranging from about 2 to about 24 hours.

According to step (st.F1) of the process, a compound of the formula (VII) as defined above may be converted into carboxamido derivatives of the formula (XVIII) as defined above. The reaction is carried out with an amine of the formula (XIV) as defined above, under basic conditions, preferably with lithium bis(trimethylsilyl)amide or sodium bis(trimethylsilyl)amide, in a suitable solvent such as tetrahydrofuran, or dioxane; at a temperature ranging from 0° C. to 40° C. and for a time ranging from about 1 to about 24 hours.

According to conversion (con.b) of the process a compound of formula (I) wherein $R_2$ is hydrogen may be converted into another compound of formula (I) wherein $R_2$ is as define above except hydrogen, by reaction with a suitable compound of formula (V) as defined above in the presence of a base such as sodium hydride or triethylamine or cesium carbonate, in a suitable solvent, for instance dichloromethane, tetrahydrofuran, dioxane or dimethylformamide, at a temperature ranging from room temperature to 100° C., so and for a time ranging from about 1 to about 12 hours.

According to conversion (con.c) of the process, the compounds of formula (I) wherein $R_2$ is hydrogen may be converted into another compound of formula (I) wherein $R_2$ is as define above except hydrogen, by reaction with an alcohol of formula (XIX) as defined above, in the presence of di-t-butylazadicarboxylate and triphenylphosphine or triphenylphosphine supported on resin, in a suitable solvent such as, for instance, tetrahydrofurane, at a temperature ranging from room temperature to 60° C. and for a time ranging from about 1 to about 12 hours.

According to conversion (con.d) of the process, the compounds of formula (Ia) wherein one of $R'_4$, $R''_4$ or $R'''_4$ is bromine, may be converted into another compound of formula (Ia) wherein one of $R'_4$, $R''_4$ or $R'''_4$ is —$NR_8R_9$ as define above by treatment with an amine of formula (XV) as define above in a suitable solvent such as tetrahydrofurane or dioxane, and in the presence of catalytic amounts of tris(dibenzilideneacetone)dipalladium, 2-dicyclohexylphosphino-2'-(N,N-dimethylamino)-biphenyl and a base such as $LiN(TMS)_2$ at a temperature ranging from room temperature to reflux and for a time ranging from 1 to about 24 hours.

According to conversion (con.e) of the process, the compounds of formula (Ia) wherein one of $R'_4$, $R''_4$ or $R'''_4$ is $NO_2$, may be converted into another compound of formula (Ia) wherein one of $R'_4$, $R''_4$ or $R'''_4$ is —$NH_2$ are as defined above in a variety of ways, according to conventional methods for reducing a nitro to an amino group. Preferably, this reaction is carried out in a suitable solvent such as, for instance, methanol, ethanol, water, tetrahydrofuran, 1,4-dioxane, N,N-dimethylformamide, acetic acid, or a mixture thereof, in the presence of a suitable reducing agent, such as, for instance, hydrogen and a hydrogenation catalyst, or by treatment with cyclohexene or cyclohexadiene, or formic acid or ammonium formate and a hydrogenation catalyst, or a metal such as iron or zinc in the presence of an inorganic acid, such as hydrochloric acid, or by treatment with tin (II) chloride, at a temperature ranging from 0° C. to reflux and for a time varying from about 1 hour to about 96 hours. The hydrogenation catalyst is usually a metal, most often palladium, which can be used as such or supported on carbon.

According to conversion (con.f) of the process, the compounds of formula (Ia) wherein one of $R'_4$, $R''_4$ or $R'''_4$ is —$NH_2$, may be converted into another compound of formula (Ia) wherein one of $R'_4$, $R''_4$ or $R'''_4$ is —$NHCOR_{10}$ as defined above, by reaction with an acid of the formula (XX) as defined above, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required, at a temperature ranging from room temperature to 60° C. and for a time ranging from about 1 to about 24 hours.

According to conversion (con.g) of the process a compound of formula (Ia) wherein one of $R'_4$, $R''_4$ or $R'''_4$ is t-butyloxycarbonyl, may be converted into another compound of formula (Ia) wherein one of $R'_4$, $R''_4$ or $R'''_4$ is —COOH by reaction in acidic condition, for example with hydrochloric acid or trifluoric acid in a suitable solvent, for instance, tetrahydrofurane or dioxane, at a temperature ranging from room temperature to 60° C. and for a time ranging from about 1 to about 12 hours.

According to conversion (con.h) of the process, the compounds of the formula (Ia) wherein one of $R'_4$, $R''_4$ or $R'''_4$ is —COOH, may be converted into another compound of formula (Ia) wherein one of $R'_4$, $R''_4$ or $R'''_4$ is a group of the formula —$CONR_8R_9$ as defined above, by reaction with an amine of the formula (XV) as defined above, under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required, at a temperature ranging from room temperature to 60° C. and for a time ranging from about 1 to about 24 hours.

According to conversion (con.i) of the process, the compounds of formula (I) wherein $R_5$, $R_6$, $R_7$ are hydrogen atoms may be converted into another compound of the formula (I) wherein one or more of $R_5$, $R_6$ or $R_7$ is halogen by carrying out the reaction in a suitable solvent such as tetrahydrofuran or dimethylformamide, using N-chlorosuccinimide or N-bromosuccinimide or N-iodosuccinimide as halogen source, at a temperature ranging from room temperature to about 100° C., and for a time of about 2 to about 48 hours and if necessary separating the resultant mixture by known methods.

According to conversion (con.l) of the process, a compound of formula (I) wherein one or more of $R_5$, $R_6$ or $R_7$ is halogen atom, may be converted into another compound of formula (I) wherein one or more of $R_5$, $R_6$, $R_7$ is a $C_1$-$C_6$ alkyl group by reaction with a suitable organo metallic compound. For example, for introducing a methyl group, the reaction may be carried out using trimethylaluminium in the presence of triphenylphosphine, in a suitable solvent such as, for instance, tetrahydrofuran, at a temperature ranging from room temperature to 60° C. and for a time ranging from about 1 to about 12 hours.

From all of the above it is clear to the skilled person that any compound of formula (I) bearing a functional group which can be further derivatized to another functional group, by working according to methods well known in the art thus leading to other compounds of formula (I), is intended to be comprised within the scope of the present invention.

According to any variant of the process for preparing the compounds of formula (I), the starting materials and any other reactants are known or easily prepared according to known methods. As an example, compounds of formula (II), (V), (IX), (XI), (XII), (XIV), (XV), (XIX), (XX), are commercially available or can be prepared as described in the following examples.

From all of the above, it is clear to the skilled person that when preparing the compounds of formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of formula (I) prepared according to the process described above are obtained as mixture of isomers, their separation using conventional techniques into the single isomers of formula (I), is within the scope of the present invention.

Conventional techniques for racemate resolution include, for instance, partitioned crystallization of diastereoisomeric salt derivatives or preparative chiral HPLC.

In addition, the compounds of formula (I) of the invention may be also prepared according to combinatorial chemistry techniques widely known in the art, for instance by accomplishing the aforementioned reactions between the several intermediates in a parallel and/or serial manner and by working under solid-phase-synthesis (SPS) conditions.

Pharmacology

The compounds of formula (I) are active as protein kinase inhibitors and are therefore useful, for instance, to restrict the unregulated proliferation of tumor cells.

In therapy, they may be used in the treatment of various tumors, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The inhibiting activity of putative MPS1 inhibitors and the potency of selected compounds was determined through the assays below described.

The short forms and abbreviations used herein have the following meaning:

| | |
|---|---|
| Ci | Curie |
| DMSO | dimethylsulfoxide |
| KDa | kiloDalton |
| microCi | microCurie |
| microg | microgram |
| microL | microliter |
| microM | micromolar |
| Et | ethyl |

Cloning, Expression and Purification of Recombinant MPSI Full Length Protein.

MPS1 full length (corresponding to residues 2-857 of the full length sequence, see Swiss-Prot accession number P33981) was PCR amplified from the full-length human MPS1 gene present in house as clone pGEX4t_MPS1. Amplification was performed using the forward oligonucleotide:

[SEQ ID NO: 1]
5'GGGGACAAGTTTGTACAAAAAAGCAGGCTTACTGGAAGTTCTGTTCCAGGGGCCCGAATCCGAGGATTTAAG

TGGCAGAG3'
and the reverse oligonucleotide:
[SEQ ID NO: 2]
5'GGGGACCACTTTGTACAAGAAAGCTGGGTTTTATTTTTTTCCCCTTTTTTTTTCAAAAGTCTTGGAGGATGA

AG3'.

Both the oligonucleotides are described in WO2009/156315 published on 30 Dec. 2009.

For cloning purposes, the oligonucleotides included attB sites in order to obtain an attB-flanked PCR product suitable for cloning using the Gateway® technology (Invitrogen). Furthermore, for purification purposes, forward primer included a protease cleavage site. The resulting PCR product was cloned in the pDONR201 plasmid and then transferred in the baculovirus expression vector pVL1393GST (Invitrogen) Gateway®-modified. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High 5 insect cells. After 72 hours of infection at 21° C., cells were recovered, pelletted and freezed at −80° C. For purification of recombinant protein, pellet was thawed, resuspended in lysis buffer (PBS, NaCl 150 mM, Glycerol 10%, CHAPS 0.1%, DTT 20 mM, protease and phosphatase inhibitors) and lysed by Gaulin. Lysate was cleared by centrifugation and loaded on a GST affinity column. After extensive wash, recombinant protein was cleaved by a specific protease and eluted by incubation.

To get a fully activated enzyme, the protein was then subjected to auto-phosphorylation in presence of ATP 1 mM at 25° C. for 2 hours in kinase buffer (Hepes pH7.5 50 mM, MgCl2 2.5 mM, MnCl2 1 mM, DTT 1 mM, phosphatase inhibitors); ATP was then removed whit a desalting column.

Biochemical Assay for Inhibitors of MPSI Kinase Activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity. Supernatant is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 l in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00

The washed resin is stable for more than one week; the stock resin is kept at 4° C. before use.

ii. Kinase Buffer (KB)

The buffer for MPS1 assay was composed of HEPES 50 mM, at pH 7.5, with 2.5 mM MgCl$_2$, 1 mM MnCl$_2$, 1 mM DTT, 3 microM NaVO$_3$, 2 mM -glycerophosphate and 0.2 mg/ml BSA iii. Assay Conditions The assay was run with a final concentration MPS1 of 5 nM, in the presence of 15 microM ATP and 1.5 nM $^{33}$P-γ-ATP; the substrate was P38-tide, used at 200 microM.

Robotized Dowex Assay

The test mix consisted of:

1) 3× Enzyme mix (done in Kinase Buffer 3×), 5 microL/well
2) 3× substrate and ATP mix (done in ddH2O), together with $^{33}$P-γ-ATP, 5 microL/well 3) 3× test compounds (diluted into ddH2O-3% DMSO)-5 microL/well See below for compound dilution and assay scheme Compound Dilution and Assay Scheme is Defined Below:

i. Dilution of Compounds

Test compounds are received as a 1 mM solution in 100% DMSO, distributed into 96 or 384 well plates:

a) for percent inhibition studies (HTS), individual dilution plates at 1 mM are diluted at a 3× concentration (30 microM) in ddH$_2$O (3% DMSO=final concentration) using a Beckman NX automated pipetting platform. The same instrument is used for distributing the diluted mother plates into the test plates.

b) for IC50 determination (KSS platform), 100 1 of each compound at 1 mM in 100% DMSO are transferred from the original plate into the first column of another 96 well plate (A1 to G1); well H1 is left empty for the internal standard inhibitor, usually staurosporine.

An automated station for serial dilutions (Biomek FX, Beckman) is used for producing 1:3 dilutions in 100% DMSO, from line A1 to A10, and for all the seven compounds in the column. Moreover, 4-5 copies of daughter plates are prepared by reformatting 5 microL of this first set of 100% DMSO dilution plates into 384 deep well-plates: one copy of the daughter plates with the serial dilutions of test compounds will be thaw the day of the experiments, reconstituted at a 3× concentration with water and used in the IC50 determination assays. In a standard experiment, the highest concentration (3×) of all compounds is 30 microM, while the lowest one is 1.5 nM.

Each 384 well-plate will contain reference wells (total enzyme activity vs. no enzymatic activity) for the Z' and signal to background evaluation.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×).

At the start of the run, the robot aspirates 5 microL of ATP mix, makes an air gap inside the tips (2 microL) and aspirates 2 microL of MPS1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

The resin suspension is very dense; in order to avoid tip clogging, wide bore tips are used to dispense it.

Another mixing cycle is performed after all the plates are stopped, this time using normal tips: the plates are then allowed to rest for about one hour in order to maximize ATP capture. At this point, 20 microL of the supernatant are transferred into 384-Optiplates (Perkin-Elmer), with 70 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for IC$_{50}$ determination in the secondary assays/hit confirmation routines.

Biochemical assays for inhibitors of other kinase activity can be performed according to known methods.

In vitro Cell Proliferation Assay

A2780 human ovarian and MCF7 human breast cancer cells (1250 cells/well) were seeded in white 384 well-plates in complete medium (RPMI 1640 or EMEM plus 10% Fetal bovine serum) and treated with compounds dissolved in 0.1% DMSO, 24 h after seeding. The cells were incubated at 37° C. and 5% CO$_2$ and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly 25 1/well reagent solution are added to each wells and after 5 minutes shacking microplates are red by Envision (PerkinElmer) luminometer. The luminescent signal is proportional to the number of cells present in culture.

Inhibitory activity was evaluated comparing treated versus control data using Assay Explorer (MDL) program. IC50 was calculated using sigmoidal interpolation curve.

Given the above inhibition assays, the compounds of formula (I) of the invention resulted to possess a good MPS1 inhibitory activity, typically with IC$_{50}$ in the range between 0.001 and 1 microM and good A2780 inhibitory activity, typically with IC$_{50}$ in the range between 0.010 and 1 microM.

The following Table A reports the experimental data of some representative compounds of the invention of formula (I) being tested on the MPS1 enzyme in the specific in vitro kinase assay above described (IC$_{50}$ microM).

TABLE A

| Compound number | MPS1 IC$_{50}$ (microM) |
| --- | --- |
| 14 | 0.041 |
| 21 | 0.022 |
| 31 | 0.067 |
| 32 | 0.110 |
| 37 | 0.084 |

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

The synthetic preparation of some compounds of formula (I) of the invention is described in the following examples. The compounds of the present invention, as prepared according to the following examples, were also characterized by $^1$H NMR or by HPLC/MS analytical data; HPLC/MS data were collected following any one of methods 1, 2, 3 and 4.

HPLC/MS Analytic Method 1

The HPLC equipment consisted of a Waters Acquity™ UPLC system equipped with a 2996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 45° C. at a flow rate of 0.8 mL/min using a BEH C18 1.7 microm Waters Acquity UPLC (2.1×50 mm) column. Mobile phase A was formic acid 0.1% pH=3.3 buffer with acetonitrile (98:2), and mobile phase B was H$_2$O/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^+$); full scan, mass range from 100 to 800 amu was set up.

HPLC/MS Analytic Method 2

The HPLC equipment consisted of a Waters 2795 Alliance HT system equipped with a 2996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 30° C. at a flow rate of 1.0 mL/min using a C18, 3 microm Phenomenex (4.6×50 mm) column. Mobile phase A was ammonium acetate 5 mM pH=5.2 buffer with acetonitrile (95:5), and mobile phase B was H$_2$O/acetonitrile (5:95); the gradient was from 10 to 90% B in 8 minutes then ramp to 100% B in 1.0 minutes. The injection volume was 10 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^-$); full scan, mass range from 100 to 800 amu was set up.

HPLC/MS Analytic Method 3

The HPLC equipment consisted of a Waters Acquity™ UPLC system equipped with a 2996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 45° C. at a flow rate of 0.8 mL/min using a BEH C18 1.7 microm Waters Acquity UPLC (2.1×50 mm) column. Mobile phase A was ammonium hydroxide 0.05% pH=10 buffer with acetonitrile (95:5), and mobile phase B was H$_2$O/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^-$); full scan, mass range from 100 to 800 amu was set up.

HPLC/MS Analytical Method 4

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 25° C. at a flow rate of 1 mL/min using a RP18 Waters X Terra (3.0×20 mm) column. Mobile phase A was ammonium hydroxide 0.05% pH=10 buffer with acetonitrile (95:5), and Mobile phase B was H$_2$O/acetonitrile (5:95); the gradient was from 10 to 90% B in 4 minutes then hold 90% B 1 minutes. The injection volume was 10 microL. The mass spectrometer was operated in positive and in negative ion mode, the capillary voltage was set up at 2.5 KV; the source temperature was 120° C.; cone was 10 V; full scan, mass range from 100 to 800 amu was set up.

Several compounds of the invention of formula (I), as prepared according to the following examples, were purified by preparative HPLC.

The operative conditions are defined below:

HPLC/MS Preparative Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 25° C. at a flow rate of 20 mL/min using a RP18 Waters X Terra 10 microm (19×250 mm) column. Mobile phase A was ammonium hydroxide 0.05% pH=10 buffer with acetonitrile (95:5), and Mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.

HPLC/MS Preparative Method 2

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 25° C. at a flow rate of 20 ml/min using a RP18 Waters X Terra 10 microm (19×250 mm) column. Mobile phase A was 0.1% trifluoro acetic acid in water/acetonitrile (95:5), and mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.

MS Exact

Exact mass data ESI(+) were obtained on a Waters Q-T of Ultima directly connected with micro HPLC 1100 Agilent as previously described (M. Colombo, F. Riccardi-Sirtori, V. Rizzo, *Rapid Commun. Mass Spectrom.* 2004, 18, 511-517).

Preparation A:

1-(5-Acetyl-1H-pyrrol-3-yl)-2,2,2-trichloro-ethanone

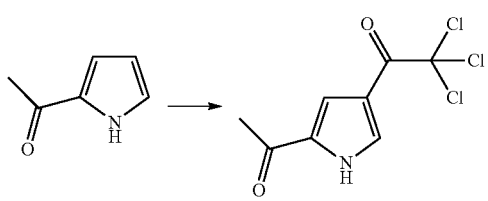

To a solution of 1-(1H-Pyrrol-2-yl)-ethanone (0.980 g, 8.98 mmol) in dichloromethane (10 mL), anhydrous aluminum trichloride (3.05 g, 22.9 mmol) were added and the suspension was vigorously stirred for 15 minutes. Trichloroacetyl chloride (1.53 mL, 13.74 mmol) in 7 mL of dichloromethane was slowly added and the mixture was then refluxed for 3 hours. The reaction mixture was cooled and poured into an iced solution of 75 mL of HCl 2N and vigorously stirred for 2 hours. Organic layer was separated and then washed with a saturated solution of NaHCO₃ (2×100 mL) and water (80 mL), dried over sodium sulfate, filtered, and concentrated in vacuo to give 1.061 g of (46%) of the title compound as a pale brown solid.

¹H NMR (400 MHz, DMSO-d6) δ ppm 2.80 (s, 3 H) 7.57 (dd, J=2.44 Hz and J=1.58 Hz, 1 H) 7.95 (dd, J=3.54 Hz and J=1.58 Hz, 1 H) 12.90 (bs, 1 H)

Preparation B:

5-Acetyl-1H-pyrrole-3-carboxylic acid ethyl ester

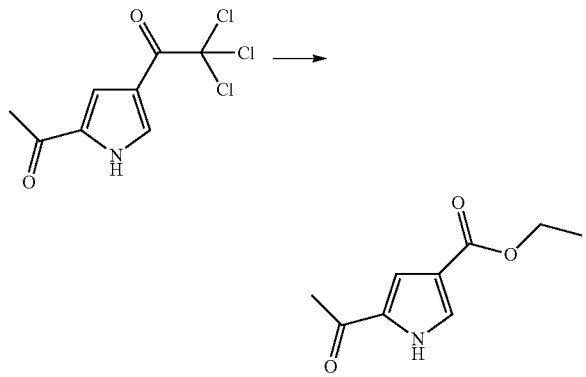

To a solution of 1-(5-Acetyl-1H-pyrrol-3-yl)-2,2,2-trichloro-ethanone (0.980 g, 3.85 mmol) in ethanol (10 mL), potassium carbonate (0.224 g, 1.62 mmol) was added and the mixture refluxed for 1 h. The mixture was cooled at room temperature and filtred through a celite pad washing with ethanol (50 mL). Organic solvent was evaporated to dryness and the residue dissolved in ethylacetate (15 mL) and washed with water (2×10 mL) and brine (5 mL), dried over sodium sulfate, filtered, and concentrated in vacuo to give 0.567 g (81%) of the title compound as a white solid.

¹H NMR (400 MHz, DMSO-d₆) δ ppm 1.27 (t, J=7.07 Hz, 3H) 2.39 (s, 3 H) 4.21 (q, J=7.07 Hz, 2H) 7.31 (dd, J=2.56 Hz and J=1.58 Hz, 1 H) 7.57 (dd, J=3.29 Hz and J=1.58 Hz, 1 H) 12.35 (bs, 1 H)

Preparation C:

5-((E)-3-Dimethylamino-acryloyl)-1H-pyrrole-3-carboxylic acid ethyl ester

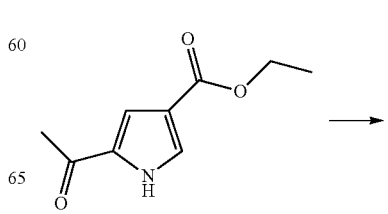

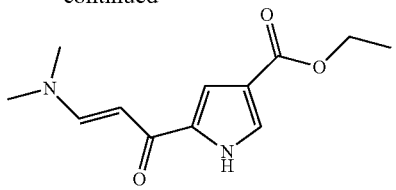

To a solution of 5-Acetyl-1H-pyrrole-3-carboxylic acid ethyl ester (0.560 g, 3.1 mmol) in 5 mL of dimethylformamide, N,N-dimethylformamide diisopropyl acetal (1.9 mL, 9.3 mmol) was added. The mixture was stirred for at 65° C. for 6 hrs. After cooling to room temperature an aqueous solution of $NaHCO_3$ 2% (30 mL) was added and extracted with ethyl acetate (50 mL×2). Organic layer was separated and washed with water (10 mL) and brine (10 mL), dried over sodium sulfate, filtered, and concentered in vacuo to give 0.531 g (72%) of the title compound.

$^1$H NMR (400 MHz, DMSO-$d_6$) δ ppm 1.26 (t, J=7.09 Hz, 3H) 2.89 (bs, 3 H) 3.10 (bs, 3 H) 4.19 (q, J=7.09 Hz, 2H) 5.70 (d, J=12.31 Hz, 1 H) 7.14 (dd, J=2.44 Hz and J=1.58 Hz, 1 H) 7.39 (dd, J=3.17 Hz and J=1.58 Hz, 1 H) 7.61 (d, J=12.31 Hz, 1 H) 11.96 (bs, 1 H)

Preparation D:

5-(2-Amino-pyrimidin-4-yl)-1H-pyrrole-3-carboxylic acid ethyl ester

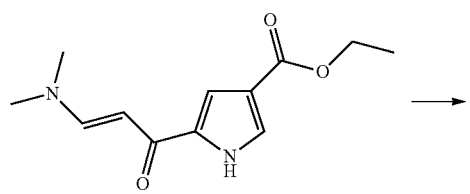

To a suspension of 5-((E)-3-Dimethylamino-acryloyl)-1H-pyrrole-3-carboxylic acid ethyl ester (0.25 g, 1.06 mmol) in 4 mL of ethanol, guanidine hydrochloride (0.121 g, 1.27 mmol) and sodium ethylate (0.086 g, 1.27 mmol) were added. The mixture was heated to 110° C. overnight. Then, a further amount of sodium ethylate (0.086 g, 1.27 mmol) was added to the mixture and heating to 115° C. was prolonged for additional 24 hours. The resulting mixture was cooled at room temperature and diluted with water (2 mL). The solid was isolated by filtration, washed with 10 mL of water, dried in a vacuum oven at 40° C. affording to give 0.197 g (80%) of the title compound.

$^1$H NMR (400 MHz, DMSO-$d_6$) δ ppm 1.27 (t, J=7.09 Hz, 3H) 4.20 (q, J=7.09 Hz, 2H) 6.39 (bs, 2 H) 6.96 (d, J=5.24 Hz, 1 H) 7.20 (dd, J=2.44 Hz and J=1.59 Hz, 1 H) 7.50 (m, 1 H) 8.19 (d, J=5.24 Hz, 1 H) 12.00 (bs, 1 H)

Preparation E:

5-((E)-3-Dimethylamino-acryloyl)-1-methyl-1H-pyrrole-3-carboxylic acid ethyl ester

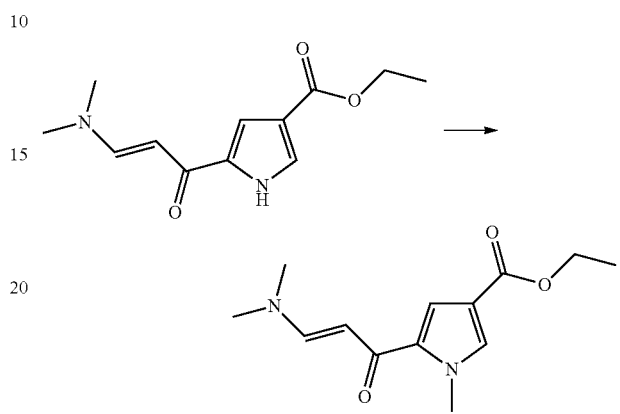

To a solution of 5-((E)-3-Dimethylamino-acryloyl)-1-methyl-1H-pyrrole-3-carboxylic acid ethyl ester (3.50 g, 14.81 mmol) in tetrahydrofuran (100 mL) cesium carbonate (9.65 g, 29.63 mmol) and methyl iodide (1.0 mL, 16.29 mmol) were added. The reaction was continued at room temperature for 1 h, tetrahydrofuran was removed under vacuo, then ethyl acetate (100 mL) was added and the organic phase washed with water (100 mL). The aqueous fraction was extracted with ethyl acetate (100 mL). The organic fractions were combined, dried over sodium sulfate, filtered, and concentered in vacuo. Purification by flash chromatography on silica gel (eluant: dichloromethane/ethanol 95/5) provided 3.15 g (85%) of the title compound as a pale yellow solid.

MS calc: 251.1390; MS found: 251.1386

Preparation F:

5-(2-Amino-pyrimidin-4-yl)-1-methyl-1H-pyrrole-3-carboxylic acid ethyl ester

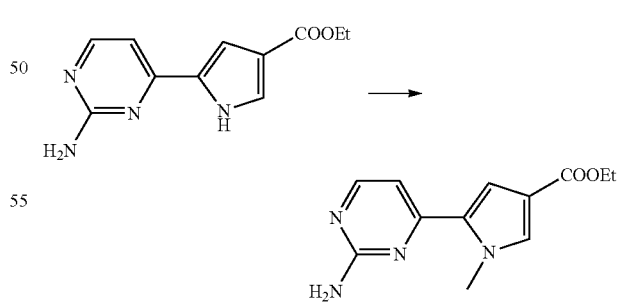

To a solution of 5-(2-amino-pyrimidin-4-yl)-1H-pyrrole-3-carboxylic acid ethyl ester (5.1 g, 21.96 mmol) in tetrahydrofuran (70 mL) and dimethylsulfoxide (15 mL) cooled in a ice-water bath, NaH (0.96 g, 24.15 mmol) and methyl iodide (1.5 mL, 24.15 mmol) were added. The reaction was continued at room temperature for 12 h, tetrahydrofuran was removed under vacuo, then dichloromethane (200 mL) was added and the organic phase washed with water (100 mL). The aqueous fraction was extracted with dichloromethane (100 mL). The organic fractions were combined, dried over sodium sulfate, filtered, and concentered in vacuo. Purification by flash chromatography on silica gel (eluant: dichloromethane/ethanol 95/5) provided 4.45 g (82%) of the title compound as a pale yellow solid.

$^1$H NMR (400 MHz, DMSO-d$_6$) δ ppm 1.23-1.29 (m, 3 H) 4.03 (s, 3 H) 4.19 (q, J=7.11 Hz, 1 H) 6.55 (s, 2 H) 6.91 (d, J=5.37 Hz, 1 H) 7.12 (d, J=1.95 Hz, 1 H) 7.61 (d, J=1.46 Hz, 1 H) 8.16 (d, J=5.24 Hz, 1H); MS (ESI): 247 [M+H]$^+$.

According to the same method, but employing the suitable starting material, the following intermediate compound was prepared:

5-(2-Amino-pyrimidin-4-yl)-1-(2-fluoro-ethyl)-1H-pyrrole-3-carboxylic acid ethyl ester $^1$H NMR (400 MHz, DMSO-d$_6$) δ ppm 1.28 (t, J=7.07 Hz, 3 H) 4.22 (q, J=7.07 Hz, 2 H) 4.72 (dt, J=47.80, 4.57 Hz, 2 H) 4.91 (dt, J=27.47, 4.56 Hz, 2 H) 6.58 (s, 2 H) 6.97 (d, J=5.24 Hz, 1 H) 7.23 (d, J=1.95 Hz, 1 H) 7.64 (d, J=1.46 Hz, 1 H) 8.17 (d, J=5.24 Hz, 1 H); MS (ESI): 279 [M+H]$^+$.

Preparation G:

5-(2-Iodo-pyrimidin-4-yl)-1-methyl-1H-pyrrole-3-carboxylic acid ethyl ester

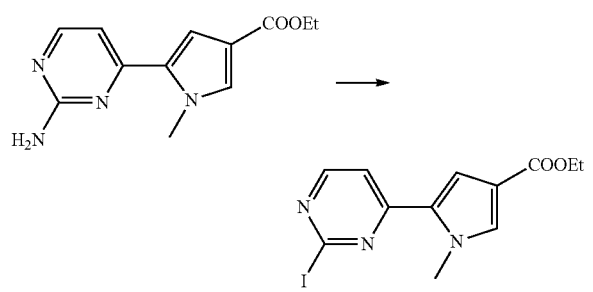

To a well stirred suspension of ethyl 5-(2-amino-pyrimidin-4-yl)-1-methyl-1H-pyrrole-3-carboxylic acid ethyl (4.55 g, 0.018 mol) in dimethoxyethane (200 mL) under N$_2$, cesium iodide (7.04 g, 0.0270 mol), bisublimated iodine (3.42 g, 0.0135 mol), copper iodide (1.54 g, 0.0081 mol) and isopentyl nitrite (5.41 mL, 0.04 mol) were added in sequence. The reaction mixture was stirred vigorously at 65-70° C. for 6 hours. After cooling in a ice-water bath, the solid was filtered off. The filtrate was diluted with dichloromethane (500 mL), washed with 30% ammonium hydroxide (150 mL), sodium thiosulphate (300 mL), brine, dried over anhydrous Na2SO4 and concentrated. Purification by flash chromatography on silica gel (eluant: dichloromethane/ethanol 95/5) afforded 1.6 g (25%) of the title compound as solid.

$^1$H NMR (300 MHz, DMSO-d$_6$) δ ppm 1.27 (t, J=7.03 Hz, 3 H) 4.00 (s, 3 H) 4.21 (q, J=7.03 Hz, 2 H) 7.44 (d, J=1.76 Hz, 1 H) 7.76 (d, J=1.76 Hz, 1 H) 7.92 (d, J=5.57 Hz, 1 H) 8.40 (d, J=5.57 Hz, 1 H); MS (ESI): 358 [M+H]$^+$.

According to the same method, but employing the suitable starting material, the following compound was prepared:

5-(2-Iodo-pyrimidin-4-yl)-1-(2-fluoro-ethyl)-1H-pyrrole-3-carboxylic acid ethyl ester $^1$H NMR (400 MHz, DMSO-d6) δ ppm 1.29 (t, J=7.07 Hz, 3 H) 4.24 (q, J=7.07 Hz, 2 H) 4.67-4.81 (m, 2 H) 4.81-4.86 (m, 2 H) 7.54 (d, J=1.83 Hz, 1 H) 7.81 (d, J=1.71 Hz, 1 H) 7.97 (d, J=5.49 Hz, 1 H) 8.42 (d, J=5.49 Hz, 1 H); MS (ESI): 390 [M+H]$^+$.

Preparation H:

5-{2-[2-Methoxy-4-(4-methyl-piperazin-1-yl)-phenylamino]-pyrimidin-4-yl}-1-methyl-1H-pyrrole-3-carboxylic acid ethyl ester

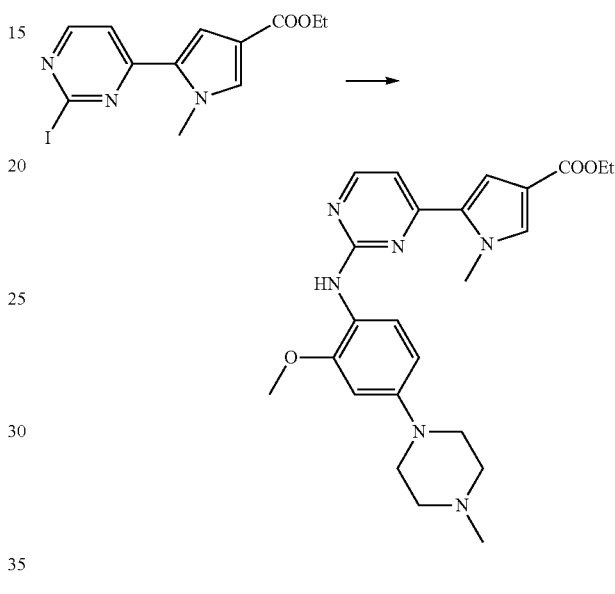

Palladium acetate [Pd(OAc)$_2$] (60 mg, 0.271 mmol), (±)-BINAP (169 mg, 0.271 mmol) and dimethylformamide (15 mL) were charged to a round-bottom flask flushed with argon. The flask was evacuated and backfilled with argon. The mixture was stirred under argon for 30 minutes and added to a mixture of 2-methoxy-4-(4-methyl-piperazin-1-yl)-phenylamine (600 mg, 2.712 mmol), 5-(2-iodo-pyrimidin-4-yl)-1-methyl-1H-pyrrole-3-carboxylic acid ethyl ester (484 mg, 1.356 mmol), and potassium carbonate (1.87 g, 13.56 mmol) in dimethylformamide (15 mL). The resulting mixture was stirred at 80° C. for 4 hours under argon. After cooling to room temperature, the reaction mixture was filtered on a pad of celite. The solvent was concentrated, the crude solid was purified by flash chromatography on silica gel (eluant: dichloromethane/methanol 95/5) to afford 160 mg (26%) of the title compound as white solid.

MS calc: 437.2296; MS found: 437.2295

According to the same method, but employing the suitable starting material, the following compounds were prepared:

5-{2-[4-(4-Methyl-piperazin-1-yl)-2-trifluoromethoxy-phenylamino]-pyrimidin-4-yl}-1H-pyrrole-3-carboxylic acid ethyl ester MS calc: 491.2013; MS found: 491.2001

5-[2-(4-tert-Butoxycarbonyl-2-methyl-phenylamino)-pyrimidin-4-yl]-1-methyl-1H-pyrrole-3-carboxylic acid ethyl ester MS calc: 437.2184; MS found: 437.2178

Preparation I:

5-{2-[2-Methoxy-4-(4-methyl-piperazin-1-yl)-phenylamino]-pyrimidin-4-yl}-1-ethyl-1H-pyrrole-3-carboxylic acid

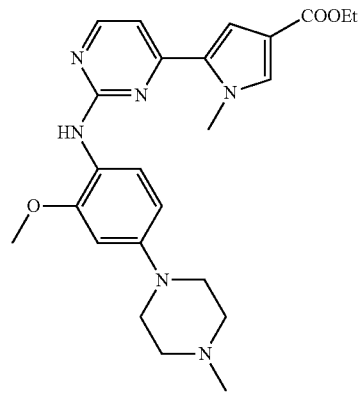

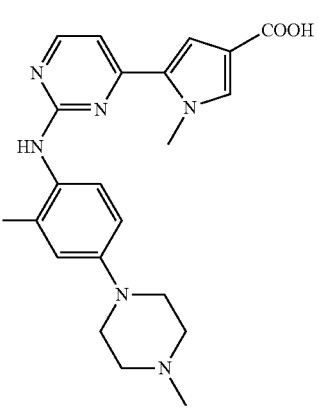

5-{2-[2-Methoxy-4-(4-methyl-piperazin-1-yl)-phenylamino]-pyrimidin-4-yl}-1-methyl-1H-pyrrole-3-carboxylic acid ethyl ester (160 mg, 0.355 mmol) was suspended in ethanol (13 mL) and treated with a 1.5 M solution of potassium hydroxide in ethanol (2.4 mL, 10 eq.) at reflux temperature for 3 hour. Solvent was evaporated to dryness and the residue dissolved in water. After treatment with acetic acid and the resulting precipitate was collected by filtration to give the title compound (150 mg, 100% yield) as a white solid.

According to this same methodology, but employing suitable substituted derivatives, the following compounds were prepared:

5-(2-Amino-pyrimidin-4-yl)-1-methyl-1H-pyrrole-3-carboxylic acid

MS calc: 219.0877; MS found: 219.0871

Example 1

5-{2-[2-Methoxy-4-(4-methyl-piperazin-1-yl)-phenylamino]-pyrimidin-4-yl}-1-methyl-1H-pyrrole-3-carboxylic acid (2,6-diethyl-phenyl)-amide

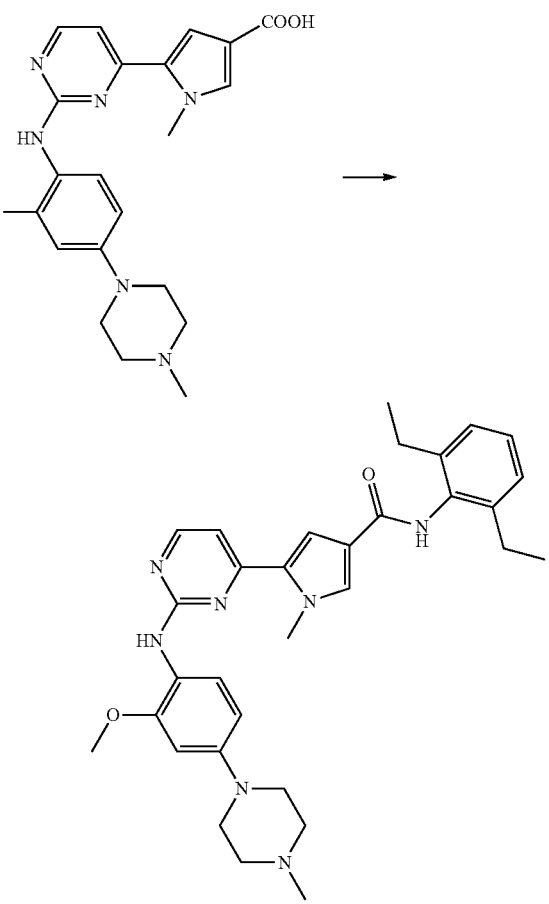

A suspension of 5-{2-[2-Methoxy-4-(4-methyl-piperazin-1-yl)-phenylamino]-pyrimidin-4-yl}-1-ethyl-1H-pyrrole-3-carboxylic acid (75 mg, 0.178 mmol) in anhydrous dimethylformamide (5 mL) was treated with N-ethyl-N,N-diisopropylamine (0.3 mL, 1.775 mmol) and TBTU (91 mg, 0.284 mmol). The mixture was then treated with 2,6-diethylaniline (0.3 mL, 1.775 mmol). The resulting mixture was stirred at 80° C. for 4 hours under argon. After cooling to room temperature, the reaction mixture was diluted with ethyl acetate (20 mL), washed with a saturated aqueous solution of sodium hydrogen carbonate (20 mL), brine, dried over anhydrous Na$_2$SO$_4$ and concentrated. Purification by flash chromatography on silica gel (eluant: dichloromethane/methanol 95/5) afforded 23 mg (23%) of the title compound.

MS calc: 554.3238; MS found: 554.3234

According to this same methodology, but employing suitable substituted derivatives, the following compounds were prepared:

5-(2-Amino-pyrimidin-4-yl)-1-methyl-1H-pyrrole-3-carboxylic acid (2,6-diethyl-phenyl)-amide MS calc: 350.1976; MS found: 350.1982

5-[2-(4-Bromo-2-methoxy-phenylamino)-pyrimidin-4-yl]-1-methyl-1H-pyrrole-3-carboxylic acid (2,6-diethyl-phenyl)-amide MS calc: 534.1499; MS found: 534.1517

5-[2-(2-Methoxy-phenylamino)-pyrimidin-4-yl]-1-methyl-1H-pyrrole-3-carboxylic acid (2,6-diethyl-phenyl)-amide MS calc: 456.2394; MS found: 456.2409

1-Methyl-5-{2-[4-(1-methyl-piperidin-4-ylcarbamoyl)-2-trifluoromethoxy-phenylamino]-pyrimidin-4-yl}-1H-pyrrole-3-carboxylic acid phenylamide MS calc: 594.2435; MS found: 594.2434

5-[2-(4-Bromo-2-methyl-phenylamino)-pyrimidin-4-yl]-1-methyl-1H-pyrrole-3-carboxylic acid (2,6-diethyl-phenyl)-amide MS calc: 518.1550; MS found: 518.1548

1-Methyl-5-(2-o-tolylamino-pyrimidin-4-yl)-1H-pyrrole-3-carboxylic acid (2,6-diethyl-phenyl)-amide MS calc: 440.2445; MS found: 440.2441

Example 2

5-{2-[4-(4-Dimethylamino-piperidin-1-yl)-2-methoxy-phenylamino]-pyrimidin-4-yl}-1-methyl-1H-pyrrole-3-carboxylic acid (2,6-diethyl-phenyl)-amide

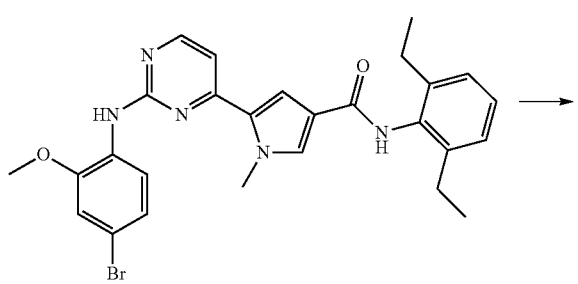

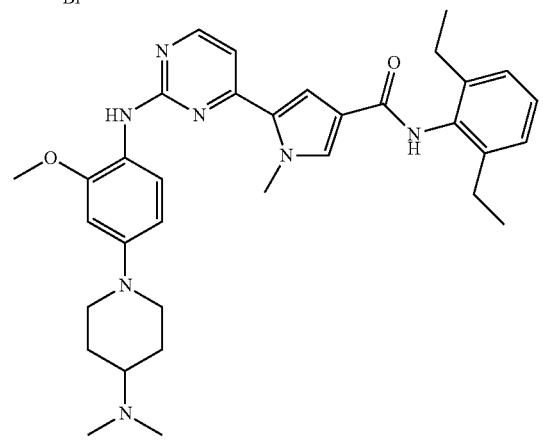

Tris(dibenzilideneacetone)dipalladium (2.6 mg, 0.003 mmol), 2-dicyclohexylphosphino-2'-(N,N-dimethylamino)-biphenyl (2.4 mg, 0.006 mmol), 5-[2-(4-Bromo-2-methoxy-phenylamino)-pyrimidin-4-yl]-1-methyl-1H-pyrrole-3-carboxylic acid (2,6-diethyl-phenyl)-amide (150 mg, 0.281 mmol) in THF (5 mL) were charged in a round-bottom flask flushed with argon. The flask was evacuated and backfilled with argon. LiN(TMS)2 solution (1M in THF, 1.7 mL) and dimethyl-piperidin-4-yl-amine (108 mg, 0.842 mmol) were added and the reaction mixture refluxed for 1 h.

The reaction mixture was then allowed to cool to room temperature and concentrated. The crude solid was purified by flash chromatography on silica gel (eluant: dichloromethane/methanol 96/4) to afford 124 mg (76% yield) of the title compound.

MS calc: 582.3551; MS found: 582.3552

According to this same methodology, but employing suitable substituted derivatives, the following compounds were prepared:

5-{2-[2-Methoxy-4-(4-methyl-[1,4]diazepan-1-yl)-phenylamino]-pyrimidin-4-yl}-1-methyl-1H-pyrrole-3-carboxylic acid (2,6-diethyl-phenyl)-amide MS calc: 568.3395; MS found: 568.3395

5-(2-{4-[(2-Dimethylamino-ethyl)-methyl-amino]-2-methoxy-phenylamino}-pyrimidin-4-yl)-1-methyl-1H-pyrrole-3-carboxylic acid (2,6-diethyl-phenyl)-amide MS calc: 556.3395; MS found: 556.3395

5-(2-{4-[(3-Dimethylamino-propyl)-methyl-amino]-2-methoxy-phenylamino}-pyrimidin-4-yl)-1-methyl-1H-pyrrole-3-carboxylic acid (2,6-diethyl-phenyl)-amide MS calc: 570.3551; MS found: 570.3546

5-(2-{4-[4-(2-Hydroxy-ethyl)-piperazin-1-yl]-2-methoxy-phenylamino}-pyrimidin-4-yl)-1-methyl-1H-pyrrole-3-carboxylic acid (2,6-diethyl-phenyl)-amide MS calc: 584.3344; MS found: 584.3347

1-Methyl-5-{2-[2-methyl-4-(4-methyl-piperazin-1-yl)-phenylamino]-pyrimidin-4-yl}-1H-pyrrole-3-carboxylic acid (2,6-diethyl-phenyl)-amide MS calc: 538.3289; MS found: 538.3279

5-{2-[4-(4-Dimethylamino-piperidin-1-yl)-2-methyl-phenylamino]-pyrimidin-4-yl}-1-methyl-1H-pyrrole-3-carboxylic acid (2,6-diethyl-phenyl)-amide MS calc: 566.3602; MS found: 566.3593

5-{2-[2-Methoxy-4-(4-pyrrolidin-1-yl-piperidin-1-yl)-phenylamino]-pyrimidin-4-yl}-1-methyl-1H-pyrrole-3-carboxylic acid (2,6-diethyl-phenyl)-amide MS calc: 608.3708; MS found: 608.3721

5-{2-[2-Methoxy-4-(1-methyl-piperidin-4-ylamino)-phenylamino]-pyrimidin-4-yl}-1-methyl-1H-pyrrole-3-carboxylic acid (2,6-diethyl-phenyl)-amide MS calc: 568.3395; MS found: 568.3379

5-{2-[4-(2-Dimethylamino-ethylamino)-2-methoxy-phenylamino]-pyrimidin-4-yl}-1-methyl-1H-pyrrole-3-carboxylic acid (2,6-diethyl-phenyl)-amide MS calc: 542.3238; MS found: 542.3235

Preparation L:

5-{2-[2-Methoxy-4-(4-methyl-piperazin-1-yl)-phenylamino]-pyrimidin-4-yl}-1H-pyrrole-3-carboxylic acid ethyl ester

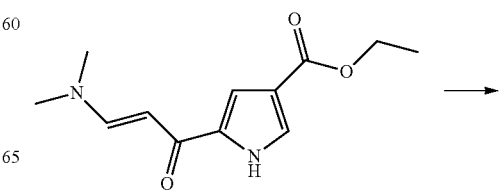

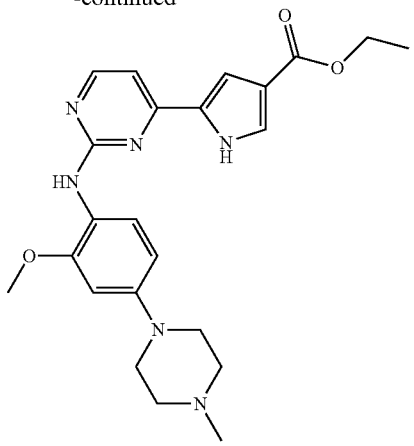

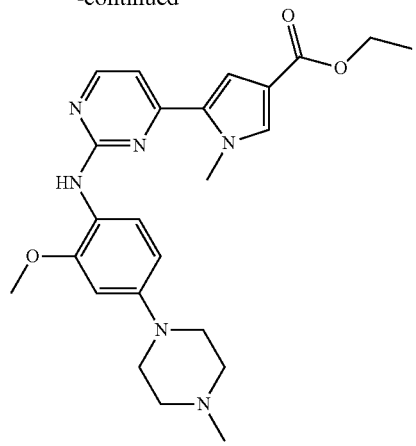

To a suspension of 5-((E)-3-Dimethylamino-acryloyl)-1H-pyrrole-3-carboxylic acid ethyl ester (1.7 g, 7.20 mmol) in 30 mL of ethanol N-[2-Methoxy-4-(4-methyl-piperazin-1-yl)-phenyl]-guanidine (1.9 g, 7.20 mmol) was added. The mixture was heated to 110° C. overnight. The resulting mixture was cooled at room temperature and diluted with water (70 mL). The solid was isolated by filtration, washed with 10 mL of water, dried in a vacuum oven at 40° C. affording to give 1.8 g (57% yield) of the title compound.

MS calc: 437.2296; MS found: 437.2295

According to this same methodology, but employing suitable substituted derivatives, the following compounds were prepared:

5-{2-[2-Methoxy-4-(4-methyl-piperazin-1-yl)-phenylamino]-pyrimidin-4-yl}-1-methyl-1H-pyrrole-3-carboxylic acid ethyl ester MS calc: 451.2452; MS found: 451.2455

1-Methyl-5-{2-[4-(1-methyl-piperidin-4-ylcarbamoyl)-2-trifluoromethoxy-phenylamino]-pyrimidin-4-yl}-1H-pyrrole-3-carboxylic acid ethyl ester MS calc: 547.2275; MS found: 547.2275

Preparation M:

5-{2-[2-Methoxy-4-(4-methyl-piperazin-1-yl)-phenylamino]-pyrimidin-4-yl}-1-methyl-1H-pyrrole-3-carboxylic acid ethyl ester

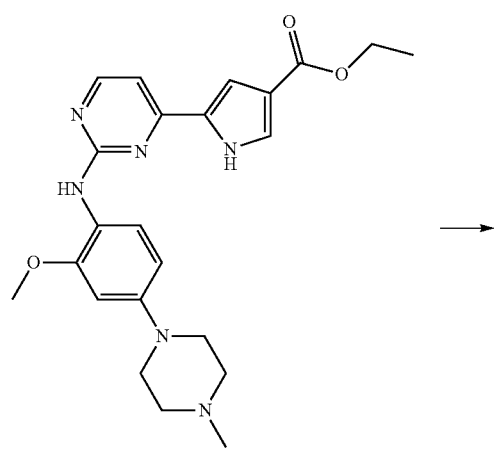

To a solution of 5-{2-[2-Methoxy-4-(4-methyl-piperazin-1-yl)-phenylamino]-pyrimidin-4-yl}-1H-pyrrole-3-carboxylic acid ethyl ester (0.5 g, 1.14 mmol) in tetrahydrofuran (25 mL) and dimethylsulfoxide (5 mL) cooled in a ice-water bath, NaH (50 mg, 1.26 mmol) and methyl iodide (0.08 mL, 1.26 mmol) were added. The reaction was continued at room temperature for 12 h, tetrahydrofuran was removed under vacuo, then dichloromethane (25 mL) was added and the organic phase washed with water (25 mL). The aqueous fraction was extracted with dichloromethane (2×20 mL). The organic fractions were combined, dried over sodium sulfate, filtered, and concentered in vacuo. Purification by flash chromatography on silica gel (eluant: dichloromethane/methanol 95/5) provided 382 mg (74%) of the title compound as a pale yellow solid.

MS calc: 451.2452; MS found: 451.2455

According to this same methodology, but employing suitable substituted derivatives, the following compounds were prepared:

5-[2-(4-Bromo-2-methoxy-phenylamino)-5-chloro-pyrimidin-4-yl]-1-(2,2,2-trifluoro-ethyl)-1H-pyrrole-3-carboxylic acid (2,6-diethyl-phenyl)-amide MS calc: 636.0983; MS found: 636.1001

5-[2-(4-Bromo-2-methoxy-phenylamino)-5-chloro-pyrimidin-4-yl]-1-(2,2,2-trifluoro-ethyl)-1H-pyrrole-3-carboxylic acid (2,6-diethyl-phenyl)-amide MS calc: 586.3301; MS found: 586.3288

Preparation N:

5-{2-[4-(4-Methyl-piperazin-1-yl)-2-trifluoromethoxy-phenylamino]-pyrimidin-4-yl}-1H-pyrrole-3-carboxylic acid ethyl ester

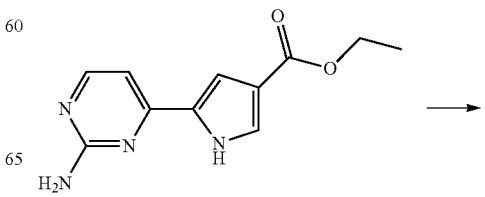

43

-continued

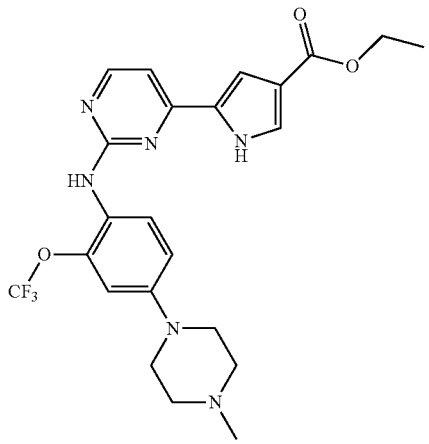

To a solution of 5-(2-amino-pyrimidin-4-yl)-1H-pyrrole-3-carboxylic acid ethyl ester (400 mg, 1.72 mmol) in dioxane (40 mL), 1-(4-iodo-3-trifluoromethoxy-phenyl)-4-methyl-piperazine (732 mg, 1.90 mmol) and cesium carbonate (1.1 g, 3.45 mmol) were added and the flask was evacuated and backfilled with argon. [Pd$_2$(dba)$_3$] (158 mg, 0.17 mmol) and Xantphos (299 mg, 0.52 mmol) were then charged and the mixture was heated at 80° C. under argon for 16 hours. After cooling to room temperature, the reaction mixture was concentrated, suspended in water (50 mL) and extracted with ethyl acetate. The organic phase was acidified on Na$_2$SO$_4$, filtered and evaporated to dryness, the crude solid was purified by flash chromatography on silica gel (eluant: dichloromethane/methanol 95/5) to afford 126 mg (15% yield) of the title compound.

MS calc: 491.2013; MS found: 491.2001

According to this same methodology, but employing suitable substituted derivatives, the following compounds were prepared:

5-[2-(4-Carbamoyl-2-methyl-phenylamino)-pyrimidin-4-yl]-1-methyl-1H-pyrrole-3-carboxylic acid (2,6-diethyl-phenyl)-amide MS calc: 483.2503; MS found: 483.2505

4-{4-[4-(2,6-Diethyl-phenylcarbamoyl)-1-methyl-1H-pyrrol-2-yl]-5-methyl-pyrimidin-2-ylamino}-3-methyl-benzoic acid tert-butyl ester MS calc: 554.3126; MS found: 554.3135

4-{4-[4-(2,6-Diethyl-phenyl carbamoyl)-1-methyl-1H-pyrrol-2-yl]-pyrimidin-2-ylamino}-3-methyl-benzoic acid tert-butyl ester MS calc: 540.2969; MS found: 540.2968

44

Example 3

5-{2-[2-Methoxy-4-(4-methyl-piperazin-1-yl)-phenylamino]-pyrimidin-4-yl}-1-methyl-1H-pyrrole-3-carboxylic acid (2,4,6-trimethyl-phenyl)-amide

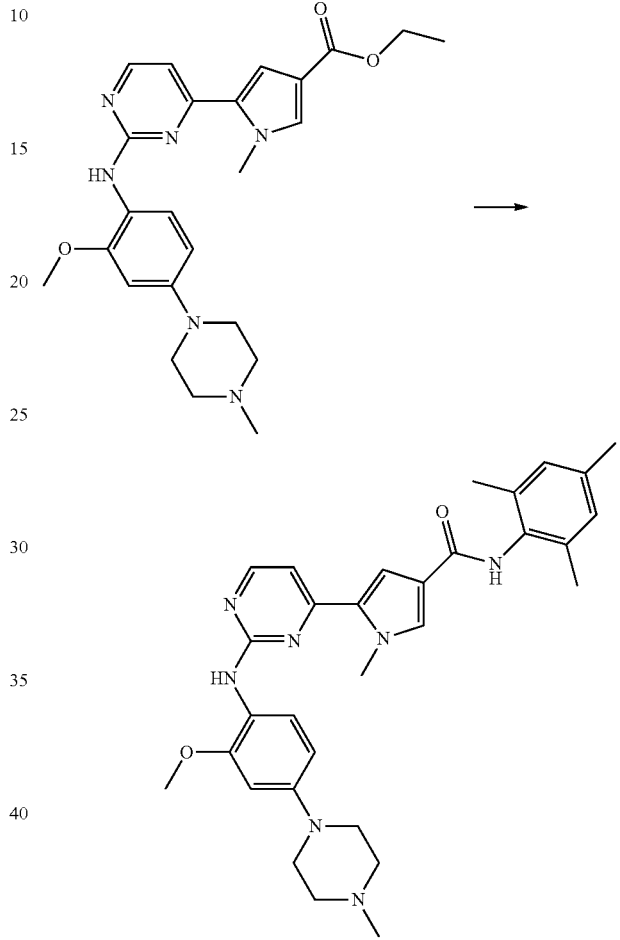

NaHMDS in THF (1.0 M, 11.0 mL, 11.0 mmol) was added over 30 min to a solution of 2,4,6-trimethylaniline (1.2 mL, 8.32 mmol) and 5-{2-[2-methoxy-4-(4-methyl-piperazin-1-yl)-phenylamino]-pyrimidin-4-yl}-1-methyl-1H-pyrrole-3-carboxylic acid ethyl ester (1.25 g, 2.77 mmol) in THF (30 mL) at 0° C. The resulting brown solution was stirred at 0° C. for 10 min and allowed to warm to room temperature over a period of 20 min. After stirring at room temperature for 4 h, the reaction was quenched by the addiction of saturated aqueous NH$_4$Cl (10 mL). The reaction was partitioned between ethyl acetate (50 mL) and water (50 mL). The aqueous layer was extracted with ethyl acetate (2×30 mL). The combined organic solution was washed with brine (50 mL), dried over Na$_2$SO$_4$, filtered and evaporated to dryness, the crude solid was purified by flash chromatography on silica gel (eluant: dichloromethane/methanol 95/5) to afford 1.10 g (72% yield) of the title compound.

MS calc: 568.3395; MS found: 568.3392

According to this same methodology, but employing suitable substituted derivatives, the following compounds were prepared:

5-{2-[2-Methoxy-4-(4-methyl-piperazin-1-yl)-phenylamino]-pyrimidin-4-yl}-1-methyl-1H-pyrrole-3-carboxylic acid (2,6-dimethyl-phenyl)-amide MS calc: 526.2925; MS found: 526.2908

5-{2-[2-Methoxy-4-(4-methyl-piperazin-1-yl)-phenylamino]-pyrimidin-4-yl}-1-methyl-1H-pyrrole-3-carboxylic acid (2-ethyl-6-methyl-phenyl)-amide MS calc: 540.3082; MS found: 540.3069

5-{2-[2-Methoxy-4-(4-methyl-piperazin-1-yl)-phenylamino]-pyrimidin-4-yl}-1-methyl-1H-pyrrole-3-carboxylic acid (2-methoxy-6-methyl-phenyl)-amide MS calc: 542.2874; MS found: 542.2876

5-{2-[2-Methoxy-4-(4-methyl-piperazin-1-yl)-phenylamino]-pyrimidin-4-yl}-1-methyl-1H-pyrrole-3-carboxylic acid (2-bromo-6-methyl-phenyl)-amide MS calc: 590.1874; MS found: 590.1874

5-{2-[2-Methoxy-4-(4-methyl-piperazin-1-yl)-phenylamino]-pyrimidin-4-yl}-1-methyl-1H-pyrrole-3-carboxylic acid (2,6-difluoro-phenyl)-amide MS calc: 534.2424; MS found: 534.2425

5-{2-[2-Methoxy-4-(4-methyl-piperazin-1-yl)-phenylamino]-pyrimidin-4-yl}-1-methyl-1H-pyrrole-3-carboxylic acid (2,4,6-trimethyl-phenyl)-amide MS calc: 540.3082; MS found: 540.3076

5-{2-[2-Methoxy-4-(4-methyl-piperazin-1-yl)-phenylamino]-pyrimidin-4-yl}-1-methyl-1H-pyrrole-3-carboxylic acid (2,4-dimethyl-pyridin-3-yl)-amide MS calc: 527.2878; MS found: 527.2875

5-{2-[2-Methoxy-4-(4-methyl-piperazin-1-yl)-phenylamino]-pyrimidin-4-yl}-1-methyl-1H-pyrrole-3-carboxylic acid (4-bromo-2-chloro-6-methyl-phenyl)-amide MS calc: 624.1484; MS found: 624.1475

5-{2-[2-Methoxy-4-(4-methyl-piperazin-1-yl)-phenylamino]-pyrimidin-4-yl}-1-methyl-1H-pyrrole-3-carboxylic acid (4-bromo-2,6-diethyl-phenyl)-amide MS calc: 632.2343; MS found: 632.2358

5-{2-[2-Methoxy-4-(4-methyl-piperazin-1-yl)-phenylamino]-pyrimidin-4-yl}-1-methyl-1H-pyrrole-3-carboxylic acid (3-chloro-2,6-diethyl-phenyl)-amide MS calc: 588.2849; MS found: 588.2850

5-{2-[2-Methoxy-4-(4-methyl-piperazin-1-yl)-phenylamino]-pyrimidin-4-yl}-1-methyl-1H-pyrrole-3-carboxylic acid (2-chloro-6-methyl-phenyl)-amide MS calc: 546.2379; MS found: 546.2360

1-Methyl-5-{2-[4-(1-methyl-piperidin-4-ylcarbamoyl)-2-trifluoromethoxy-phenylamino]-pyrimidin-4-yl}-1H-pyrrole-3-carboxylic acid (2,6-diethyl-phenyl)-amide MS calc: 650.3061; MS found: 650.3069

Example 4

5-{5-Bromo-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide

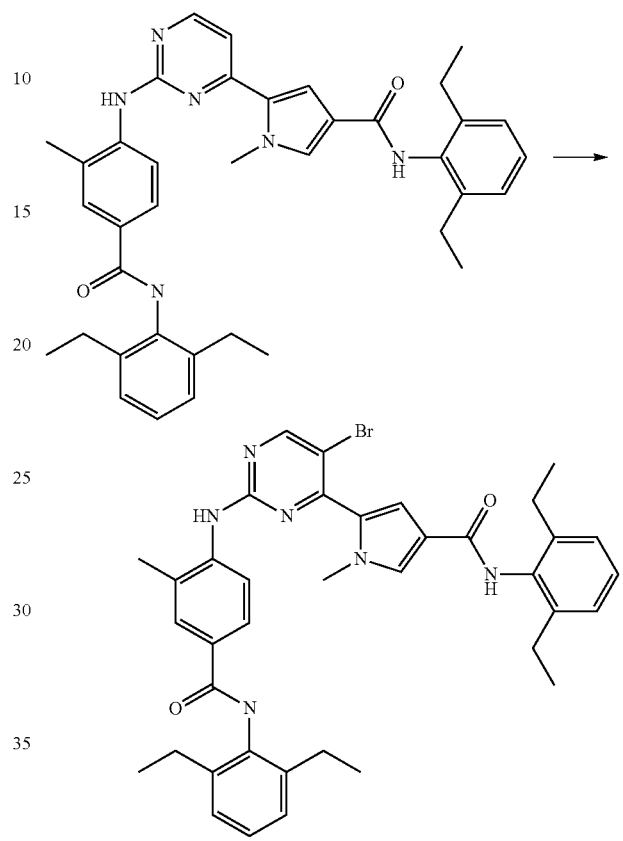

A solution of 5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide (100 mg, 0.1626 mmol) and NBS (29 mg, 0.1626 mmol) in 7.5 mL of DMF was stirred at room temperature for 1 h. The mixture was then diluted with AcOEt and washed with water. The organic layer was dried over $Na_2SO_4$ and the solvent removed under reduced pressure. The target product was purified by preparative HPLC (39.8 mg, 35%, Exact Mass: calculated 693.2547, found 693.2548) as well as 2-bromo-5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide (24.7 mg, 22%, Exact Mass: calculated 693.2547, found 693.2556.) and 2-bromo-5-{5-bromo-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide (8.1 mg, 6.5%, Exact Mass: calculated 771.1652, found 771.1653).

According to the same method, but employing the suitable starting material, the following compounds were prepared:

5-(2-Amino-5-chloro-pyrimidin-4-yl)-1H-pyrrole-3-carboxylic acid ethyl ester

MS calc: 267.0644; MS found: 267.0643

5-{5-Chloro-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide.

MS calc: 649.3053; MS found: 649.3053.

2-Chloro-5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide.

MS calc: 649.3053; MS found: 649.3074.

2-Chloro-5-{5-chloro-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide.

MS calc: 683.2663; MS found: 683.2653.

5-[2-(4-Carbamoyl-2-methyl-phenylamino)-5-chloro-pyrimidin-4-yl]-1-methyl-1H-pyrrole-3-carboxylic acid (2,6-diethyl-phenyl)-amide.

MS calc: 517.2114; MS found: 517.2122.

5-[2-(4-Carbamoyl-2-methyl-phenylamino)-pyrimidin-4-yl]-2-chloro-1-methyl-1H-pyrrole-3-carboxylic acid (2,6-diethyl-phenyl)-amide.

MS calc: 517.2114; MS found: 517.2106.

5-[2-(4-Carbamoyl-2-methyl-phenylamino)-pyrimidin-4-yl]-4-chloro-1-methyl-1H-pyrrole-3-carboxylic acid (2,6-diethyl-phenyl)-amide.

MS calc: 517.2114; MS found: 517.2119.

5-[2-(4-Carbamoyl-2-methyl-phenylamino)-5-chloro-pyrimidin-4-yl]-2-chloro-1-methyl-1H-pyrrole-3-carboxylic acid (2,6-diethyl-phenyl)-amide.

MS calc: 551.1724; MS found: 551.1727.

5-{5-Bromo-2-[2-methoxy-4-(4-methyl-piperazin-1-yl)-phenylamino]-pyrimidin-4-yl}-1-methyl-1H-pyrrole-3-carboxylic acid (2,6-diethyl-phenyl)-amide Preparation O:

5-(2-Amino-5-methyl-pyrimidin-4-yl)-1-methyl-1H-pyrrole-3-carboxylic acid (2,6-diethyl-phenyl)-amide

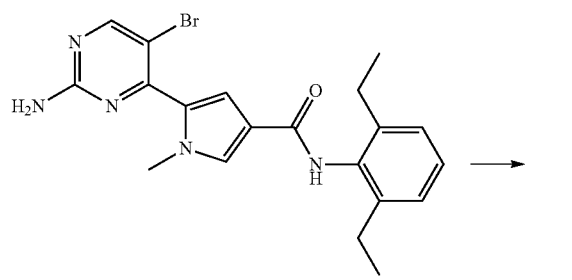

To a solution of 5-(2-Amino-5-bromo-pyrimidin-4-yl)-1-methyl-1H-pyrrole-3-carboxylic acid (2,6-diethyl-phenyl)-amide (83.7 mg, 0.1954 mmol) in 4 mL of dry THF, AlMe$_3$ (1M in toluene, 0.488 mL, 0.977 mmol) and Pd(PPh$_3$)$_4$ (22.6 mg, 0.0195 mmol) were added under argon. The mixture was heated at 65° C. for 1 h. After dilution with water and extraction with CH$_2$Cl$_2$ the organic layer was dried over Na$_2$SO$_4$ and concentrated under reduced pressure. The crude was treated with Et$_2$O affording 58.8 mg (83%) of the desired product.

MS calc: 364.2132; MS found: 364.2134.

Example 5

4-{4-[4-(2,6-Diethyl-phenylcarbamoyl)-1-methyl-1H-pyrrol-2-yl]-5-methyl-pyrimidin-2-ylamino}-3-methyl-benzoic acid

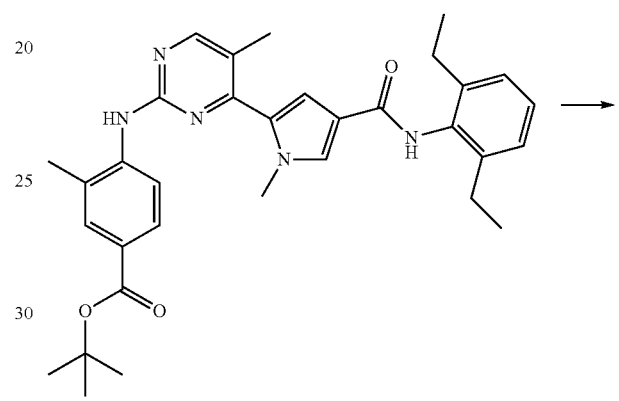

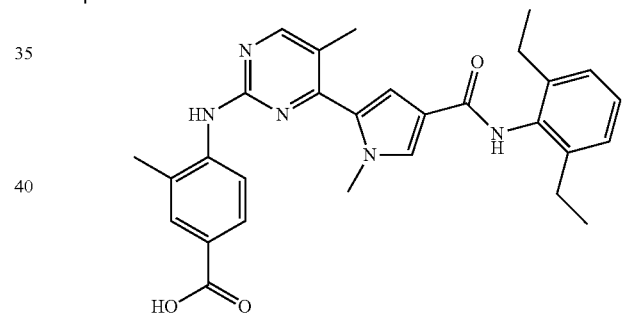

To a solution of 4-{4-[4-(2,6-Diethyl-phenylcarbamoyl)-1-methyl-1H-pyrrol-2-yl]-5-methyl-pyrimidin-2-ylamino}-3-methyl-benzoic acid tert-butyl ester (438 mg, 0.790 mmol) in dichloromethane (20 ml), trifluoroacetic acid (1.2 ml) was added. The mixture was stirred at room temperature overnight. Water was added and the mixture extracted with ethylacetate. The organic solvent evaporated to dryness to give 393 mg of the title compound in quantitative yield.

MS calc: 498.2500; MS found: 498.2504

According to this same methodology, but employing suitable substituted derivatives, the following compounds were prepared:

4-{4-[4-(2,6-Diethyl-phenylcarbamoyl)-1-methyl-1H-pyrrol-2-yl]-pyrimidin-2-ylamino}-3-methyl-benzoic acid MS calc: 484.2343; MS found: 484.2346

Example 6

5-{2-[4-(4-Dimethylamino-piperidine-1-carbonyl)-2-methyl-phenylamino]-5-methyl-pyrimidin-4-yl}-1-methyl-1H-pyrrole-3-carboxylic acid (2,6-diethyl-phenyl)-amide

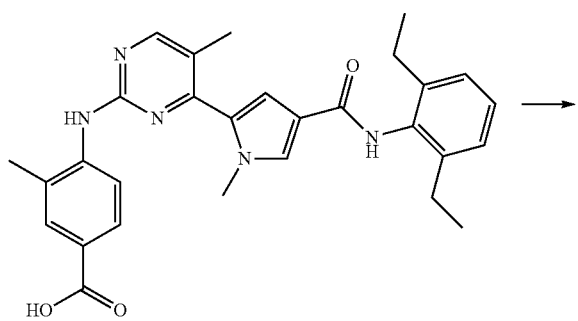

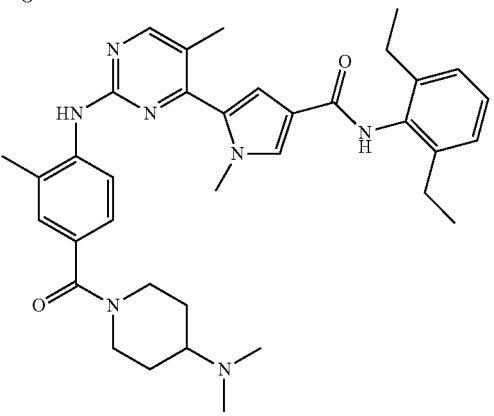

A suspension of 4-{4-[4-(2,6-Diethyl-phenylcarbamoyl)-1-methyl-1H-pyrrol-2-yl]-5-methyl-pyrimidin-2-ylamino}-3-methyl-benzoic acid (177 mg, 0.356 mmol) in anhydrous dimethylformamide (10 mL) was treated with N-ethyl-N,N-diisopropylamine (0.60 mL, 3.55 mmol) and TBTU (183 mg, 0.569 mmol). The mixture was then treated with dimethylpiperidin-4-yl-amine (91 mg, 0.711 mmol). The reaction was stirred at room temperature for 24 h. The reaction was diluted with water and the resulting precipitate was collected by filtration. The crude solid was purified by flash chromatography on silica gel (eluant: dichloromethane/methanol 9/1) to afford 118 mg of the title compound.

MS calculated: 608.3708; MS found: 608.3711

According to this same methodology, but employing suitable substituted derivatives, the following compounds were prepared:

5-[2-(4-Carbamoyl-2-methyl-phenylamino)-5-methyl-pyrimidin-4-yl]-1-methyl-1H-pyrrole-3-carboxylic acid (2,6-diethyl-phenyl)-amide MS calculated: 497.2660; MS found: 497.2664

5-{2-[4-(2,6-Diethyl-phenylcarbamoyl)-2-methyl-phenylamino]-pyrimidin-4-yl}-1-methyl-1H-pyrrole-3-carboxylic acid (2,6-diethyl-phenyl)-amide MS calculated: 615.3442; MS found: 615.3435

5-[2-(4-Dimethylcarbamoyl-2-methyl-phenylamino)-pyrimidin-4-yl]-1-methyl-1H-pyrrole-3-carboxylic acid (2,6-diethyl-phenyl)-amide MS calculated: 511.2816; MS found: 511.2815

1-Methyl-5-[2-(2-methyl-4-methylcarbamoyl-phenylamino)-pyrimidin-4-yl]-1H-pyrrole-3-carboxylic acid (2,6-diethyl-phenyl)-amide MS calculated: 497.2660; MS found: 497.2664

5-{2-[4-(2-Dimethylamino-ethylcarbamoyl)-2-methyl-phenylamino]-pyrimidin-4-yl}-1-methyl-1H-pyrrole-3-carboxylic acid (2,6-diethyl-phenyl)-amide MS calculated: 554.3238; MS found: 554.3241

5-{2-[4-(4-Dimethylamino-piperidine-1-carbonyl)-2-methyl-phenylamino]-pyrimidin-4-yl}-1-methyl-1H-pyrrole-3-carboxylic acid (2,6-diethyl-phenyl)-amide MS calculated: 594.3551; MS found: 594.3564

1-Methyl-5-{2-[2-methyl-4-((R)-2-pyrrolidin-1-ylmethyl-pyrrolidine-1-carbonyl)-phenylamino]-pyrimidin-4-yl}-1H-pyrrole-3-carboxylic acid (2,6-diethyl-phenyl)-amide MS calculated: 620.3708; MS found: 620.3725

Preparation P:

4-(4-Methyl-piperazin-1-yl)-2-trifluoromethoxy-phenylamine

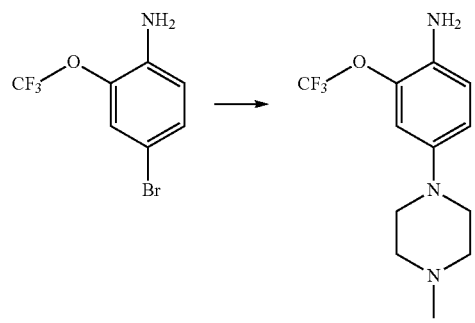 [SMILES: Nc1ccc(Br)cc1OC(F)(F)F ; CN1CCN(c2ccc(N)c(OC(F)(F)F)c2)CC1]

Tris(dibenzilideneacetone)dipalladium (1.1 g, 1.2 mmol), 2-dicyclohexylphosphino-2'-(N,N-dimethylamino)-biphenyl (0.94 g, 2.4 mmol), 4-bromo-2-trifluoromethoxy-phenylamine (30.7 g, 120 mmol) in THF (50 mL) were charged in a round-bottom flask flushed with argon. The flask was evacuated and backfilled with argon. LiN(TMS)$_2$ solution (1M in THF, 288 mL) and N-methylpiperazine (26.7 mL, 194 mmol) were added and the reaction refluxed for 1 h. The reaction mixture was then allowed to cool to room temperature and filtered through a pad of celite. The organic phase was concentrated, the residue dissolved in DCM (200 ml) and washed with water (1×100 ml). The organic phases were dried over anhydrous Na$_2$SO$_4$, the solvent evaporated in vacuo and the crude solid was purified by flash chromatography on silica gel (eluant: DCM/EtOH 90/10) to afford 23 g of 4-(4-methyl-piperazin-1-yl)-2-trifluoromethoxy-phenylamine (70% yield) as a light brown powder.

MS calc: 276.1318; MS found: 276.1320

According to this same methodology, but employing suitable substituted derivatives, the following compound was prepared:

4-(4-Methyl-piperazin-1-yl)-2-methoxy-phenylamine

MS calc: 222.1601; MS found: 222.1596

Preparation Q:

N-[4-(4-Methyl-piperazin-1-yl)-2-trifluoromethoxy-phenyl]-guanidine

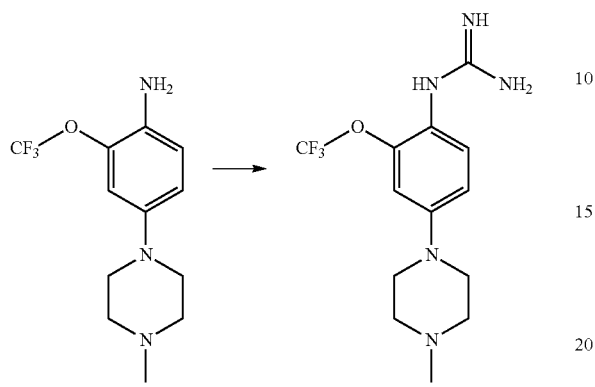

To a solution of 4-(4-methyl-piperazin-1-yl)-2-trifluoromethoxy-phenylamine (275 mg, 1 mmol) in HCl 6N (1 mL), cyanamide (336 mg, 8.0 mmol) was added and the reaction was stirred at 60° C. for 1 h. The mixture was cooled down to room temperature, diluted with water (3 mL), extracted with DCM (10 mL). NaOH 2N was added to pH>11.

The aqueous phase was extracted with $Et_2O$ (3×10 mL), dried over sodium sulfate and concentrated. The residue was crystallized from diethyl ether to give the title compound (240 mg, 76% yield) as a white solid.

MS calc: 318.1536; MS found: 318.1526

According to this same methodology, but employing suitable substituted derivatives, the following compounds were prepared:

N-[4-(4-Methyl-piperazin-1-yl)-2-methoxy-phenyl]-guanidine
MS calc: 264.1819; MS found: 264.1817

N-[4-(tert-butylcarboxamido)-2-methoxy-phenyl]-guanidine
MS calc: 266.1499; MS found: 266.1491

Preparation R:

4-Iodo-3-methoxybenzoic acid

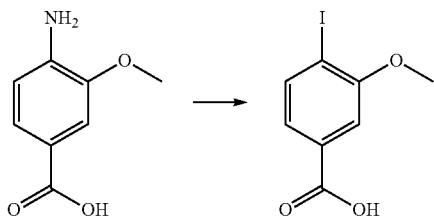

To a solution of 4-amino-3-methoxybenzoic acid (5 mg, 29.9 mmol) in $H_2O$ (30 mL) and HCl 37% (30 mL) at 0° C., a solution of $NaNO_2$ (2.27 g, 32.9 mmol) in $H_2O$ (10 mL) was slowly added. The solution obtained was then stirred for 20 minutes and then added at 0° C. to a solution of KI (34.75 g, 7 mmol) in $H_2O$ (10 mL). The mixture was stirred for 3 hours. After cooling in an ice-water bath, the solid was filtered off. The filtrate was diluted with ethyl acetate, washed with 10% sodium methabisulphite, dried over anhydrous Na2SO4 and concentrated to give 3.7 g of the title compound (46% yield).

$^1$H NMR (400 MHz, DMSO-$d_6$) δ ppm: 3.90 (s, 3 H) 7.31(dd, J 1.71 Hz and J 8.05 Hz, 1 H), 7.43 (d, J 1.71 Hz, 1 H), 7.92 (d, J 8.05 Hz, 1 H), 13.15 (b.s., 1H).

Preparation S:

tert-Buthyloxy 4-Iodo-3-methoxybenzoate

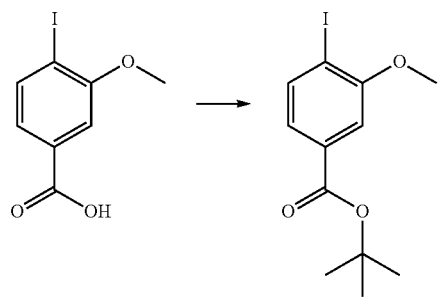 [SMILES: COc1cc(C(=O)O)ccc1I ; COc1cc(C(=O)OC(C)(C)C)ccc1I]

To a solution of 4-iodo-3-methoxybenzoic acid (2.7 g, 11 mmol) in dichloromethane (40 mL) and tert-buthanol (10 mL), di-tert-buthyldicarbonate (4.2 g, 19.2 mmol) and a catalytic amount of 4-dimethylaminopyridine were added. The mixture was heated at reflux for 24 hours. The mixture was cooled down to room temperature, and the solvent evaporated to dryness. The residue was crystallized from diethyl ether to give the title compound (2.3 g, 62% yield) as a white solid.

$^1$H NMR (400 MHz, DMSO-$d_6$) δ ppm: 1.55 (s, 9 H) 3.89 (s, 3 H) 7.27(dd, J 1.71 Hz and J 8.05 Hz, 1 H), 7.38 (d, J 1.71 Hz, 1 H), 7.92 (d, J 8.05 Hz, 1 H).

According to this same methodology, but employing suitable substituted derivatives, the following compounds were prepared:

4-[Iodo-3-(trifluoromethoxy)phenyl]4-methylpiperazine
MS calc: 387.0176; MS found: 387.0182

4-Iodo-N-(1-methylpiperidin-yl)-3-(trifluoromethoxy)benzamide

MS calc: 429.0282; MS found: 429.0289

Preparation T:

4-Iodo-3-methoxy-N-(1-methylpiperidin-yl)benzamide

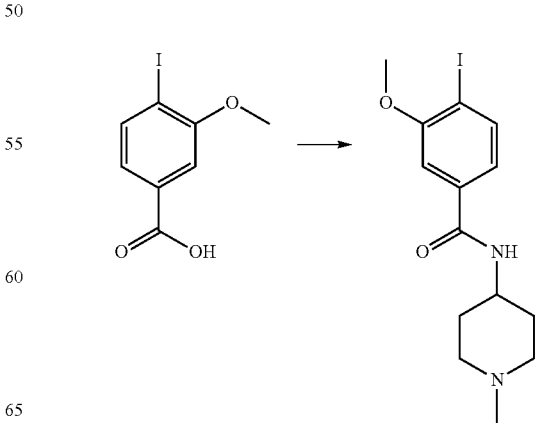

A solution of 4-iodo-3-methoxybenzoic acid (250 mg, 0.90 mmol) in anhydrous dimethylformamide (8 mL) was treated with N-ethyl-N,N-diisopropylamine (0.63 mL, 3.6 mmol) and TBTU (404 mg, 1.26 mmol). The mixture was then treated with 1-methylpiperidin-4-amine (0.160 ml, 1.26 mmol). The reaction was stirred at room temperature for 24 h. The reaction was diluted with water and the resulting precipitate was collected by filtration to afford the title compound (250 mg, 71% yield).

MS calc: 375.0564; MS found: 375.0576

According to the same method, but employing the suitable starting material, the following compound was prepared:

4-Iodo-3-methyl-benzamide $^1$H NMR (400 MHz, DMSO-$d_6$) δ ppm 2.41 (s, 3H) 7.36 (bs, 1 H) 7.40 (dd, J=8.17 Hz and J=1.95 Hz, 1 H) 7.80 (d, J=1.95 Hz, 1 H) 7.90 (d, J=8.17 Hz, 1 H) 7.95 (bs, 1 H).

The invention claimed is:

1. A compound of the formula (I):

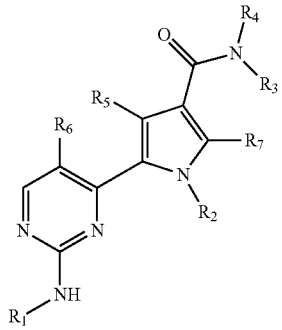

wherein
$R_1$ is a phenyl group;
$R_2$ is hydrogen atom or straight or branched $C_1$-$C_6$ alkyl;
$R_3$ is an aryl group;
$R_4$ is hydrogen atom;
$R_5$ and $R_7$ are each independently hydrogen or halogen atom;
$R_6$ is hydrogen, halogen atom or a $C_1$-$C_6$ alkyl group;
wherein the groups phenyl, aryl and straight or branched $C_1$-$C_6$ alkyl may be optionally substituted,
provided that the compound 1-methyl-5-{2-[4-(1-methyl-piperidin-4-ylcarbamoyl)-2-trifluoromethoxy-phenylamino]-pyrimidin-4-yl}-1H-pyrrole-3-carboxylic acid o-tolylamide is excluded;
and stereoisomers, tautomers, hydrates, solvates, N-oxides and pharmaceutically acceptable salts thereof.

2. A compound of formula (I) according to claim 1 wherein $R_1$ is a phenyl of the formula:

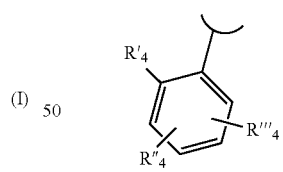

wherein $R'_4$, $R''_4$ and $R'''_4$ are independently hydrogen or halogen atom, or nitro, cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_6$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfony, arylaminosulfonyl, heterocyclylaminosulfonyl, arylthio, alkylthio, phosphonate or alkylphosphonate group.

3. A compound of formula (I) according to claim 2 wherein R'$_4$ is not hydrogen atom.

4. A compound according to claim 1 of formula (Ia):

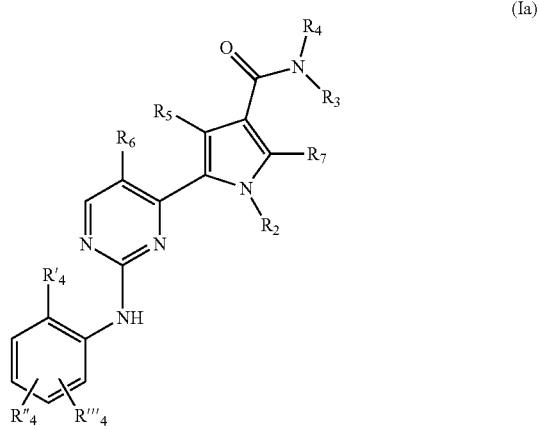

(Ia)

wherein
R$_6$ is hydrogen, halogen atom or a methyl group, or a pharmaceutically acceptable salt thereof.

5. A compound of formula (I) according to claim 1 which is selected from:

5-[2-(4-Carbamoyl-2-methyl-phenylamino)-pyrimidin-4-yl]-1-methyl-1H-pyrrole-3-carboxylic acid (2,6-diethyl-phenyl)-amide;

5-{2-[2-Methoxy-4-(4-methyl-piperazin-1-yl)-phenylamino]-pyrimidin-4-yl}-1-methyl-1H-pyrrole-3-carboxylic acid (2,6-diethyl-phenyl)-amide;

1-Methyl-5-{2-[4-(1-methyl-piperidin-4-ylcarbamoyl)-2-trifluoromethoxy-phenylamino]-pyrimidin-4-yl}-1H-pyrrole-3-carboxylic acid phenylamide;

5-[2-(4-tert-Butoxycarbonyl-2-methyl-phenylamino)-pyrimidin-4-yl]-1-methyl-1H-pyrrole-3-carboxylic acid ethyl ester;

5-{2-[4-(2,6-Diethyl-phenylcarbamoyl)-2-methyl-phenylamino]-pyrimidin-4-yl}-1-methyl-1H-pyrrole-3-carboxylic acid (2,6-diethyl-phenyl)-amide;

4-{4-[4-(2,6-Diethyl-phenylcarbamoyl)-1-methyl-1H-pyrrol-2-yl]-pyrimidin-2-ylamino}-3-methyl-benzoic acid;

2-Chloro-5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

2-Chloro-5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

2-Chloro-5-{5-chloro-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

2-Bromo-5-{2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

5-{5-Bromo-2-[4-(2,6-diethyl-phenylcarbamoyl)-2-methyl-phenylamino]-pyrimidin-4-yl}-1-methyl-1H-pyrrole-3-carboxylic acid (2,6-diethyl-phenyl)-amide;

2-Bromo-5-{5-bromo-2-[4-(2,6-diethyl-phenylcarbamoyl)-2-methyl-phenylamino]-pyrimidin-4-yl}1-methyl-1H-pyrrole-3-carboxylic acid (2,6-diethyl-phenyl)-amide;

5-[2-(4-Dimethylcarbamoyl-2-methyl-phenylamino)-pyrimidin-4-yl]-1-methyl-1H-pyrrole-3-carboxylic acid (2,6-diethyl-phenyl)-amide;

1-Methyl-5-[2-(2-methyl-4-methylcarbamoyl-phenylamino)-pyrimidin-4-yl]1H-pyrrole-3-carboxylic acid (2,6-diethyl-phenyl)-amide;

5-{2-[4-(2-Dimethylamino-ethylcarbamoyl)-2-methyl-phenylamino]-pyrimidin-4-yl}-1-methyl-1H-pyrrole-3-carboxylic acid (2,6-diethyl-phenyl)-amide;

5-{2-[4-(4-Dimethylamino-piperidine-1-carbonyl)-2-methyl-phenylamino]-pyrimidin-4-yl}-1-methyl-1H-pyrrole-3-carboxylic acid (2,6-diethyl-phenyl)-amide;

1-Methyl-5-{2-[2-methyl-4-((R)-2-pyrrolidin-1-ylmethyl-pyrrolidine-1-carbonyl)-phenylamino]-pyrimidin-4-yl}1H-pyrrole-3-carboxylic acid (2,6-diethyl-phenyl)-amide;

5-[2-(4-Carbamoyl-2-methyl-phenylamino)-pyrimidin-4-yl]-2-chloro-1-methyl-1H-pyrrole-3-carboxylic acid (2,6-diethyl-phenyl)-amide;

5-[2-(4-Carbamoyl-2-methyl-phenylamino)-5-chloro-pyrimidin-4-yl]-1-methyl-1H-pyrrole-3-carboxylic acid (2,6-diethyl-phenyl)-amide;

5-[2-(4-Carbamoyl-2-methyl-phenylamino)-5-chloro-pyrimidin-4-yl]-2-chloro-1-methyl-1H-pyrrole-3-carboxylic acid (2,6-diethyl-phenyl)-amide;

5-[2-(4-Carbamoyl-2-methyl-phenylamino)-pyrimidin-4-yl]-4-chloro-1-methyl-1H-pyrrole-3-carboxylic acid (2,6-diethyl-phenyl)-amide;

5-[2-(4-Bromo-2-methoxy-phenylamino)-pyrimidin-4-yl]-1-methyl-1H-pyrrole-3-carboxylic acid (2,6-diethyl-phenyl)-amide;

5-{2-[4-(4-Dimethylamino-piperidin-1-yl)-2-methoxy-phenylamino]-pyrimidin-4-yl}-1-methyl-1H-pyrrole-3-carboxylic acid (2,6-diethyl-phenyl)-amide;

5-[2-(2-Methoxy-phenylamino)-pyrimidin-4-yl]-1-methyl-1H-pyrrole-3-carboxylic acid (2,6-diethyl-phenyl)-amide;

5-{2-[2-Methoxy-4-(4-methyl-[1,4]diazepan-1-yl)-phenylamino]-pyrimidin-4-yl}-1-methyl-1H-pyrrole-3-carboxylic acid (2,6-diethyl-phenyl)-amide;

4-{4-[4-(2,6-Diethyl-phenylcarbamoyl)-1-methyl-1H-pyrrol-2-yl]-5-methyl-pyrimidin-2-ylamino}-3-methyl-benzoic acid tert-butyl ester;

5-(2-{4-[(2-Dimethylamino-ethyl)-methyl-amino]-2-methoxy-phenylamino}-pyrimidin-4-yl)-1-methyl-1H-pyrrole-3-carboxylic acid (2,6-diethyl-phenyl)-amide;

4-{4-[4-(2,6-Diethyl-phenylcarbamoyl)-1-methyl-1H-pyrrol-2-yl]-5-methyl-pyrimidin-2-ylamino}-3-methyl-benzoic acid;

5-[2-(4-Carbamoyl-2-methyl-phenylamino)-5-methyl-pyrimidin-4-yl]-1-methyl-1H-pyrrole-3-carboxylic acid (2,6-diethyl-phenyl)-amide;

5-{2-[4-(4-Dimethylamino-piperidine-l-carbonyl)-2-methyl-phenylamino]-5-methyl-pyrimidin-4-yl}-1-methyl-1H-pyrrole-3-carboxylic acid (2,6-diethyl-phenyl)-amide;

5-(2-{4-[(3-Dimethylamino-propyl)-methyl-amino]-2-methoxy-phenylamino}-pyrimidin-4-yl)-1-methyl-1H-pyrrole-3-carboxylic acid (2,6-diethyl-phenyl)-amide;

5-[2-(4-Bromo-2-methoxy-phenylamino)-5-chloro-pyrimidin-4-yl]-1-(2,2,2-trifluoro-ethyl)-1H-pyrrole-3-carboxylic acid (2,6-diethyl-phenyl)-amide;

1-(2-Fluoro-ethyl)-5-{2-[2-methoxy-4-(4-methyl-piperazin-1-yl)-phenylamino]-pyrimidin-4-yl}-1H-pyrrole-3-carboxylic acid (2,6-diethyl-phenyl)-amide;

5-{5-Bromo-2-[2-methoxy-4-(4-methyl-piperazin-1-yl)-phenylamino]-pyrimidin-4-yl}-1-methyl-1H-pyrrole-3-carboxylic acid (2,6-diethyl-phenyl)-amide;
5-(2-{4-[4-(2-Hydroxy-ethyl)-piperazin-1-yl]-2-methoxy-phenylamino}-pyrimidin-4-yl)-1-methyl-1H-pyrrole-3-carboxylic acid (2,6-diethyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2-chloro-6-methyl-phenyl)-amide;
5-[2-(4-Bromo-2-methyl-phenylamino)-pyrimidin-4-yl]-1-methyl-1H-pyrrole-3-carboxylic acid (2,6-diethyl-phenyl)-amide;
1-Methyl-5-{2-[2-methyl-4-(4-methyl-piperazin-1-yl)-phenylamino]-pyrimidin-4-yl}-1H-pyrrole-3-carboxylic acid (2,6-diethyl-phenyl)-amide;
5-{2-[4-(4-Dimethylamino-piperidin-1-yl)-2-methyl-phenylamino]-pyrimidin-4-yl}-1-methyl-1H-pyrrole-3-carboxylic acid (2,6-diethyl-phenyl)-amide;
1-Methyl-5-(2-o-tolylamino-pyrimidin-4-yl)-1H-pyrrole-3-carboxylic acid (2,6-diethyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2,6-dimethyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2-ethyl-6-methyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2-methoxy-6-methyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2-bromo-6-methyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2,6-difluoro-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2,4,6-trimethyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2,4-dimethyl-pyridin-3-yl)-amide;
5-{2-[2-Methoxy-4-(4-methyl-piperazin-1-yl)-phenylamino]-pyrimidin-4-yl}-1-methyl-1H-pyrrole-3-carboxylic acid (4-bromo-2-chloro-6-methyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (4-bromo-2,6-diethyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (3-chloro-2,6-diethyl-phenyl)-amide;
5-{2-[2-Methoxy-4-(4-methyl-piperazin-1-yl)-phenylamino]-pyrimidin-4-yl}-1-methyl-1H-pyrrole-3-carboxylic acid (2,6-diethyl-4-methyl-phenyl)-amide;
5-{2-[2-Methoxy-4-(4-pyrrolidin-1-yl-piperidin-1-yl)-phenylamino]-pyrimidin-4-yl}1-1-methyl-1H-pyrrole-3-carboxylic acid (2,6-diethyl-phenyl)-amide;
5-{2-[2-Methoxy-4-(1-methyl-piperidin-4-ylamino)-phenylamino]-pyrimidin-4-yl}-1-methyl-1H-pyrrole-3-carboxylic acid (2,6-diethyl-phenyl)-amide;
5-{2-[4-(2-Dimethylamino-ethylamino)-2-methoxy-phenylamino]-pyrimidin-4-yl}-1-methyl-1H-pyrrole-3-carboxylic acid (2,6-diethyl-phenyl)-amide and 1-Methyl-5-{2-[4-(1-methyl-piperidin-4-ylcarbamoyl)-2-trifluoromethoxy-phenylamino]-pyrimidin-4-yl}-1H-pyrrole-3-carboxylic acid (2,6-diethyl-phenyl)-amide.

6. A process for preparing a compound of formula (I) or the pharmaceutically acceptable salts thereof, as defined in claim 1, which process comprises:

st.A1) reacting a compound of the formula (II):

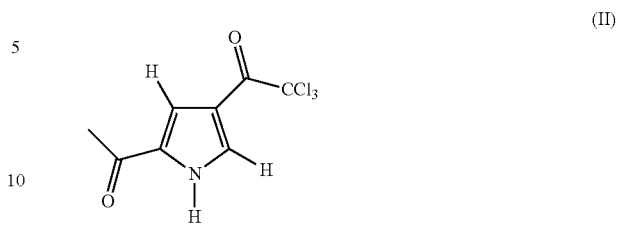

with a base in a $C_1$-$C_4$ alcohol;

st.A2) reacting the resultant compound of formula (IV):

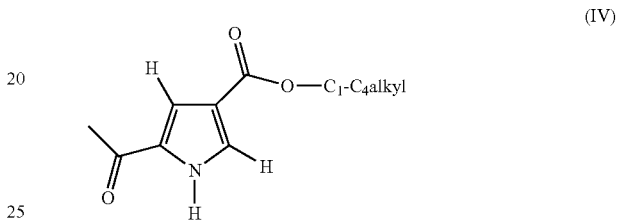

with dimethylformamide-di-tert-butylacetale, dimethylformamide-diisopropylacetale or dimethylformamide-diethylacetale;

optionally converting the resultant compound of the formula (VI):

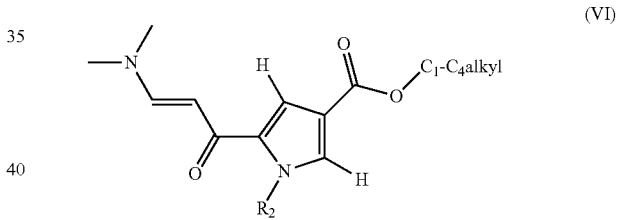

wherein $R_2$ is H, by means of alkylation with a compound of the formula (V):

$$R_2—Y \quad (V)$$

wherein Y is a suitable leaving group, or halogen atom, and $R_2$ is as defined in claim 1 but not hydrogen, into a compound of the formula (VI) wherein $R_2$ is not hydrogen atom;

st.A3) reacting the compound of the formula (VI) as defined above according to any one of the following alternative steps (st.A3a), (st.A3b) or (st. A3c):

st.A3a) either with guanidine, and then reacting the resultant compound of the formula (VII):

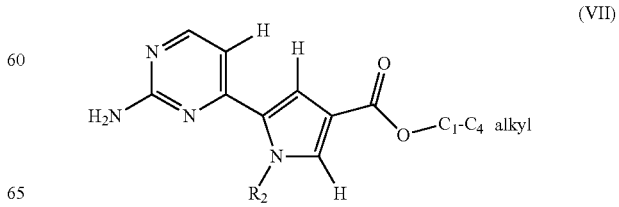

wherein R₂ is as defined above, with iso-amylnitrite and diiodomethane or cesium iodide, in the presence of iodine and CuI and then reacting the resultant compound of the formula (VIII):

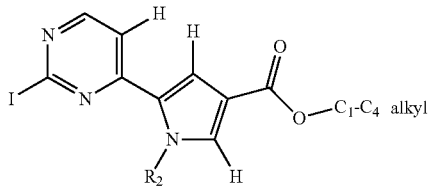
(VIII)

wherein R₂ is as defined above with a compound of formula (IX): R₁—NH₂ wherein R₁ is as defined in claim 1;
st.A3b) or with a guanidine derivative of formula (XI):

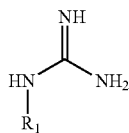
(XI)

wherein R₁ is as defined above;
st.A3c) or with guanidine, and then reacting the resultant compound of the formula (VII) as defined above with a compound of the formula (XII): R₁—I wherein R₁ is as defined above;
st.A4) reacting the resultant compound of the formula (X):

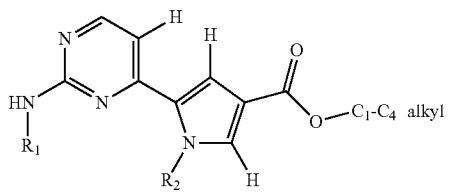
(X)

wherein R₁ and R₂ are as defined above in acidic or basic condition;
st.A5) reacting the resultant compound of the formula (XIII) or a salt thereof:

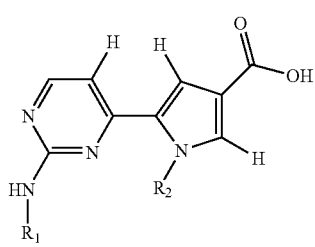
(XIII)

wherein R₁ and R₂ are as defined above, with an amine of the formula (XIV):

R₃—NH—R₄ (XIV)

wherein R₃ and R₄ are as defined in claim 1, in presence of the suitable condensing agents; and optionally converting the resultant compound of the formula (I):

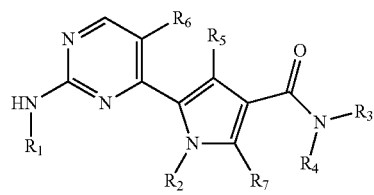
(I)

wherein R₁, R₂, R₃ and R₄ are as defined above and R₅, R₆ and R₇ are hydrogen atoms, into a compound of the formula (I), wherein not all of R₅ R₆ and R₇ are hydrogen atoms; and,
if desired, converting a compound of formula (I) into a pharmaceutically acceptable salt thereof or converting a salt into the free compound (I).

7. A process for preparing a compound of formula (I) or the pharmaceutically acceptable salts thereof, as defined in claim 1, which process comprises:
either
st.D1) reacting a compound of formula (XVIII):

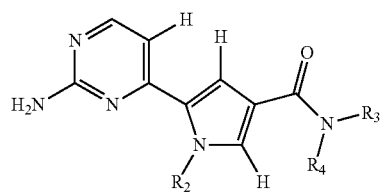
(XVIII)

wherein R₂, R₃ and R₄ are as defined in claim 1, with a compound of the formula (XII) R₁—I wherein R₁ is as defined in claim 1,
or
st.F1) reacting a compound of formula (VII):

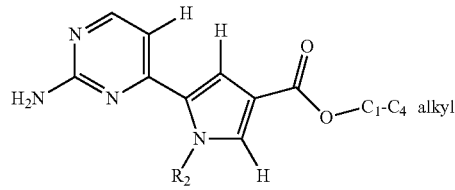
(VII)

wherein R₂ is as defined in claim 1 but not hydrogen, with an amine of formula (XIV), R3—NH—R₄,
wherein R₃ and R₄ are as defined in claim 1, in presence of a strong base;
then reacting the resultant compound of the formula (XVIII) as defined above with iso-amylnitrite and diiodomethane or cesium iodide, in the presence of iodine and CuI; finally reacting the resultant compound of the formula (XVI):

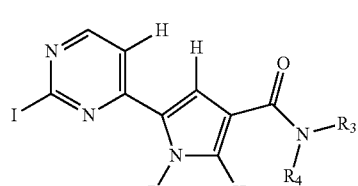
(XVI)

wherein R₂, R₃ and R₄ are as defined above, with an arylamine of formula (IX): R₁—NH₂ wherein $R_1$ is as defined in claim 1;

and optionally converting the resultant compound of the formula (I) as defined above wherein $R_5$, $R_6$ and $R_7$ are hydrogen atoms, into a compound of the formula (I), wherein not all of $R_5$, $R_6$ and $R_7$ are hydrogen atoms; and, if desired, converting a compound of formula (I) into a pharmaceutically acceptable salt thereof or converting a salt into the free compound (I).

8. A process for preparing a compound of formula (I) as defined in claim 1, characterized in that the conversion of a compound of formula (I) into another compound of formula (I) is carried out with one of the following methods:

conv.b and c) converting a compound of formula (I) wherein $R_2$ is hydrogen and $R_1$, $R_3$, $R_4$, $R_5$ and $R_6$ are as defined in claim 1 into a compound of formula (I) wherein $R_2$ is not hydrogen by reaction either with a compound of the formula (V), or with an alcohol of formula $R_2$—OH (XIX) wherein $R_2$ is as defined above but not hydrogen;

conv.d) converting a compound of the formula (Ia) wherein one of $R'_4$, $R''_4$ or $R'''_4$ is Br, into a compound of formula (Ia) wherein one of $R'_4$, $R''_4$ or $R'''_4$ is a group of the formula —$NR_8R_9$ wherein $R_8$ and $R_9$ are each independently selected from a group consisting of: hydrogen atom, $C_1$-$C_6$ alkyl, polyfluorinated alkyl, alkenyl, alkynyl, hydroxyalkyl, aryl, arylalkyl, heterocyclyl, $C_3$-$C_6$ cycloalkyl, alkylamino, arylamino, heterocyclylamino, by treatment with an amine of the formula $R_8R_9$—NH (XV), wherein $R_8$ and $R_9$ are as defined above;

conv.e) converting a compound of formula (Ia) wherein one of $R'_4$, $R''_4$ or $R'''_4$ is a nitro group into a compound of formula (Ia) wherein one of $R'_4$, $R''_4$ or $R'''_4$, is an amino group (—$NH_2$), by conventional methods of reduction;

conv. f) converting a compound of formula (Ia) wherein one of $R'_4$, $R''_4$ or $R'''_4$ is an amino group (—$NH_2$), into a compound of formula (Ia) wherein one of $R'_4$, $R''_4$ or $R'''_4$ is a group—$NHCOR_{10}$, wherein $R_{10}$ is selected from a group consisting of: $C_1$-$C_6$ alkyl, polyfluorinated alkyl, alkenyl, alkynyl, aryl, arylalkyl, heterocyclyl, $C_3$-$C_6$ cycloalkyl, alkylamino, arylamino, heterocyclylamino, by treatment with an acid of the formula $R_{10}$—COOH (XX), wherein $R_{10}$ is as defined above, in the presence of suitable condensing agents;

conv.g) converting a compound of formula (Ia) wherein one of $R'_4$, $R''_4$ or $R'''_4$ is t-butyloxycarbonyl in acidic condition, into a compound of formula (Ia) wherein one of $R'_4$, $R''_4$ or $R'''_4$ is —COOH;

conv.h) converting a compound of formula (Ia) wherein one of $R'_4$, $R''_4$ or $R'''_4$ is COOH, into a compound of formula (Ia) wherein one of $R'_4$, $R''_4$ or $R'''_4$ is a group —$CONR_8R_9$ wherein $R_8$ and $R_9$ are as defined above, by treatment with an amine of the formula (XV) as defined above in the presence of the suitable condensing agents;

conv.i) converting a compound of formula (I) wherein $R_5$, $R_6$ and $R_7$ are hydrogen atoms into a compound of formula (I) wherein one or more of $R_5$, $R_6$ and $R_7$ are halogen atoms, by reaction with N-halogen-succinimide;

conv.l) converting a compound of formula (I) wherein one or more of $R_5$, $R_6$ and $R_7$ are halogen into a compound of formula (I) wherein one or more of $R_5$, $R_6$ and $R_7$ are a $C_1$—$C_6$ alkyl group, by treatment with a suitable organo metallic compound.

9. A pharmaceutical composition comprising a therapeutically effective amount of a compound of formula (I), as defined in claim 1, and at least one pharmaceutically acceptable carrier or diluent.

10. A pharmaceutical composition according to claim 9 further comprising one or more chemotherapeutic agents.

11. A product comprising a compound of formula (I) as defined in claim 1 or a pharmaceutical composition thereof as defined in claim 11, and one or more chemotherapeutic agents, as a combined preparation for simultaneous, separate or sequential use in anticancer therapy.

12. A compound of formula (I), as defined in claim 1, for use as a medicament.

13. An in vitro method for inhibiting protein kinase activity, wherein the protein kinase is selected from the group consisting of human MPS1(TTK), PLK family members, protein kinase C in different isoforms, Met, PAK-4, PAK-5, STLK-2, DDR-2, Aurora 1, Aurora 2, Bub-1, Chk1, Chk2, HER2, raf1, MEK1, MAPK, EGF-R, PDGF-R, FGF-R, IGF-R, PI3K, weel kinase, Src, Abl, Akt, MAPK, ILK, MK-2, IKK-2, Cdc7, and Nek, which comprises contacting the kinase with an effective amount of a compound of formula (I) as defined in claim 1.

* * * * *